US011058287B2

(12) United States Patent
Uchida

(10) Patent No.: US 11,058,287 B2
(45) Date of Patent: Jul. 13, 2021

(54) OPTICAL SYSTEM FOR STEREOSCOPIC VISION AND IMAGE PICKUP APPARATUS USING THE SAME

(71) Applicant: OLYMPUS CORPORATION, Hachioji (JP)

(72) Inventor: Yoshihiro Uchida, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/706,324

(22) Filed: Dec. 6, 2019

(65) Prior Publication Data

US 2020/0107707 A1 Apr. 9, 2020

Related U.S. Application Data

(63) Continuation of application No. PCT/JP2017/024301, filed on Jul. 3, 2017.

(51) Int. Cl.
*A61B 1/00* (2006.01)
*H04N 13/239* (2018.01)
(Continued)

(52) U.S. Cl.
CPC ...... *A61B 1/00188* (2013.01); *A61B 1/00193* (2013.01); *G02B 30/22* (2020.01);
(Continued)

(58) Field of Classification Search
CPC .............. H04N 13/239; H04N 13/243; H04N 5/232125; H04N 5/2254;
(Continued)

(56) References Cited

U.S. PATENT DOCUMENTS 5,557,454 A 9/1996 Takahashi
5,743,846 A * 4/1998 Takahashi .......... A61B 1/00193
600/111

(Continued)

FOREIGN PATENT DOCUMENTS

JP H735989 A 2/1995
JP H07261094 A 10/1995
(Continued)

OTHER PUBLICATIONS

Related U.S. Appl. No. 16/574,651; First Named Inventor: Yoshihiro Uchida; Title: "Stereoscopic-Vision Endoscope Optical System and Endoscope Using the Same"; filed Sep. 18, 2019.
(Continued)

*Primary Examiner* — Brian P Yenke
*Assistant Examiner* — Sean N. Haiem
(74) *Attorney, Agent, or Firm* — Holtz, Holtz & Volek PC

(57) ABSTRACT

An optical system for stereoscopic vision includes a first optical system and a second optical system. Each of the first optical system and the second optical system includes a stop and a plurality of lens units. The plurality of lens units includes at least one movable lens unit which moves at the time of focusing, and at least focusing to a near point and focusing to a far point is carried out by movement of the movable lens unit. At the time of focusing to a near point, both a first entrance pupil and a second entrance pupil are positioned on an image side of positions at the time of focusing to a far point. Here, the first entrance pupil is an entrance pupil of the first optical system, and the second entrance pupil is an entrance pupil of the second optical system.

30 Claims, 24 Drawing Sheets

(51) Int. Cl.
| | |
|---|---|
| *H04N 5/232* | (2006.01) |
| *G02B 30/22* | (2020.01) |
| *H04N 5/225* | (2006.01) |

(52) U.S. Cl.
CPC ..... *H04N 5/2254* (2013.01); *H04N 5/232125* (2018.08); *H04N 13/239* (2018.05); *H04N 2005/2255* (2013.01); *H04N 2213/001* (2013.01)

(58) Field of Classification Search
CPC ..... H04N 2005/2255; H04N 2213/001; G02B 23/26; G02B 23/24; G02B 30/22; G02B 13/00; G02B 13/18; A61B 1/00188; A61B 1/00193; A61B 1/00096
USPC ........... 348/47, 51, 240.3; 600/166; 345/156
See application file for complete search history.

(56) References Cited

U.S. PATENT DOCUMENTS

| | | | |
|---|---|---|---|
| 5,971,915 A | 10/1999 | Yamamoto et al. | |
| 5,976,071 A | 11/1999 | Sekiya | |
| 6,306,082 B1 | 10/2001 | Takahashi et al. | |
| 6,338,711 B1 | 1/2002 | Sekiya et al. | |
| 6,364,888 B1 | 4/2002 | Niemeyer et al. | |
| 6,383,131 B1 | 5/2002 | Yamamoto et al. | |
| 6,396,627 B1 * | 5/2002 | Tachihara | G02B 21/22 348/42 |
| 6,414,791 B1 * | 7/2002 | Sugawara | G03B 35/10 359/464 |
| 6,517,479 B1 | 2/2003 | Sekiya | |
| 6,720,988 B1 | 4/2004 | Gere et al. | |
| 6,976,956 B2 | 12/2005 | Takahashi et al. | |
| 7,564,619 B2 | 7/2009 | Uzawa et al. | |
| 8,221,304 B2 | 7/2012 | Shioda et al. | |
| 8,345,084 B2 | 1/2013 | Namii et al. | |
| 8,648,896 B2 | 2/2014 | Takahashi | |
| 8,743,185 B2 | 6/2014 | Yamaguchi et al. | |
| 8,934,169 B2 | 1/2015 | Mirlay | |
| 10,274,717 B2 | 4/2019 | Togino | |
| 2001/0055062 A1 | 12/2001 | Shioda et al. | |
| 2002/0055795 A1 | 5/2002 | Niemeyer et al. | |
| 2002/0082476 A1 | 6/2002 | Takahashi et al. | |
| 2003/0029463 A1 | 2/2003 | Niemeyer | |
| 2005/0020876 A1 | 1/2005 | Shioda et al. | |
| 2005/0027397 A1 | 2/2005 | Niemeyer | |
| 2006/0092273 A1 | 5/2006 | Gere et al. | |
| 2006/0146009 A1 * | 7/2006 | Syrbe | G06F 1/1686 345/156 |
| 2006/0274433 A1 * | 12/2006 | Kamo | G02B 15/177 359/793 |
| 2007/0285508 A1 | 12/2007 | Gere et al. | |
| 2008/0174861 A1 * | 7/2008 | Uzawa | G02B 21/22 359/377 |
| 2010/0208046 A1 | 8/2010 | Takahashi | |
| 2012/0008194 A1 * | 1/2012 | Mizuta | G02B 21/22 359/377 |
| 2012/0075448 A1 | 3/2012 | Namii et al. | |
| 2012/0113233 A1 * | 5/2012 | Yamaguchi | H04N 13/239 348/49 |
| 2013/0044369 A1 | 2/2013 | Mirlay | |
| 2013/0070123 A1 * | 3/2013 | Imaoka | G02B 27/0025 348/240.3 |
| 2013/0113891 A1 * | 5/2013 | Mayhew | H04N 13/239 348/47 |
| 2013/0242412 A1 * | 9/2013 | Uchida | G02B 13/0045 359/714 |
| 2014/0300711 A1 * | 10/2014 | Kroon | H04N 13/144 348/51 |
| 2015/0036146 A1 * | 2/2015 | Staloff | A61B 5/0066 356/479 |
| 2016/0131869 A1 * | 5/2016 | Liao | G02B 13/0045 250/208.1 |
| 2016/0266370 A1 * | 9/2016 | Uchida | G02B 27/10 |
| 2016/0320606 A1 | 11/2016 | Togino | |
| 2017/0168264 A1 * | 6/2017 | Chen | G02B 13/0045 |
| 2017/0235123 A1 * | 8/2017 | Kamo | G02B 9/34 359/738 |
| 2018/0120554 A1 | 5/2018 | Fukushima | |
| 2018/0231748 A1 * | 8/2018 | Chang | G02B 9/64 |
| 2020/0008660 A1 | 1/2020 | Uchida et al. | |
| 2020/0018935 A1 | 1/2020 | Uchida | |

FOREIGN PATENT DOCUMENTS

| | | |
|---|---|---|
| JP | H07261099 A | 10/1995 |
| JP | H08304714 A | 11/1996 |
| JP | H116967 A | 1/1999 |
| JP | 2001075011 A | 3/2001 |
| JP | 2002011022 A | 1/2002 |
| JP | 3283084 B2 | 3/2002 |
| JP | 2008170803 A | 7/2008 |
| JP | 4750175 B2 | 8/2011 |
| JP | 2012113281 A | 6/2012 |
| JP | 2013524285 A | 6/2013 |
| JP | 2014110910 A | 6/2014 |
| JP | 2014160240 A | 9/2014 |
| JP | 2014174390 A | 9/2014 |
| WO | 2011049195 A1 | 4/2011 |
| WO | 2017033234 A1 | 3/2017 |

OTHER PUBLICATIONS

Related U.S. Appl. No. 16/583,057; First Named Inventor: Yoshihiro Uchida; Title: "Optical System For Stereoscopic Vision and Endoscope Using the Same"; filed Sep. 25, 2019.
Related U.S. Appl. No. 16/745,733; First Named Inventor: Yoshihiro Uchida; Title: "Optical System for Stereoscopic Vision and Image Pickup Apparatus Using the Same"; filed Jan. 17, 2020.
International Search Report (ISR) dated Sep. 26, 2017 (and English translation thereof), issued in International Application No. PCT/JP2017/024301.
Written Opinion of the International Searching Authority dated Sep. 26, 2017 issued in International Application No. PCT/JP2017/024301.
International Preliminary Report on Patentability (IPRP) dated Jan. 16, 2020 (and English translation thereof), issued in International Application No. PCT/JP2017/024301.

* cited by examiner

AS
FIY 0.92

DT
FIY 0.92

Ta,IH 0

Sa,IH 0

Ta,IH 0.5

Sa,IH 0.5

Ta,IH 0.7

Sa,IH 0.7

Ta,IH 1.0

Sa,IH 1.0

------- 0.486
—·— 0.588
------ 0.656

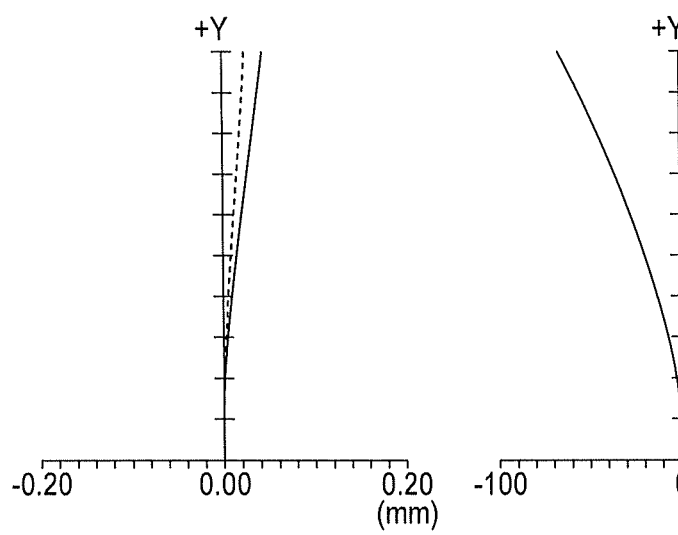
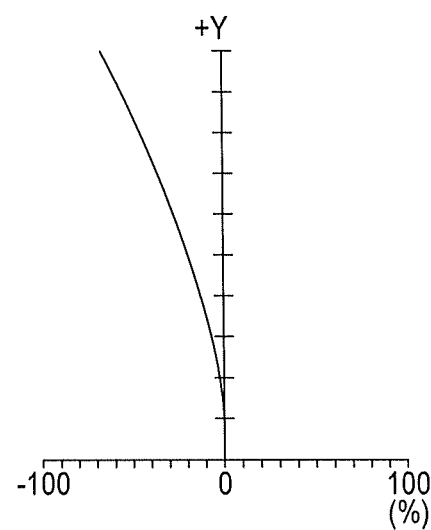
FIG.13A AS FIY 0.92
FIG.13B DT FIY 0.92
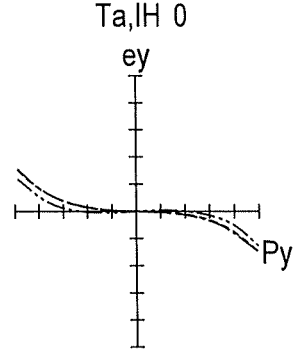 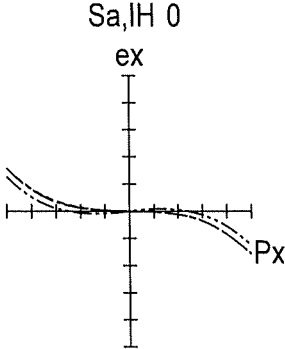 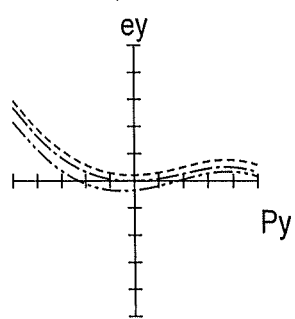 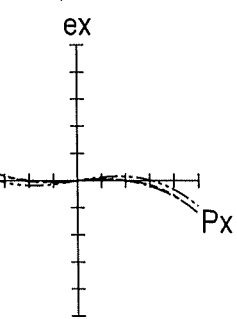
FIG.13C Ta,IH 0
FIG.13D Sa,IH 0
FIG.13E Ta,IH 0.5
FIG.13F Sa,IH 0.5
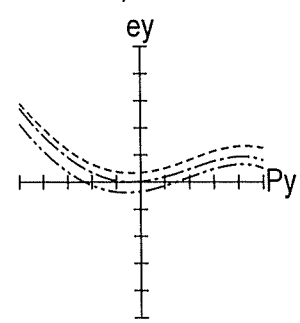 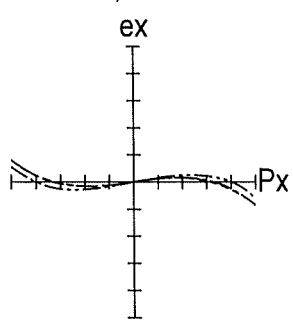 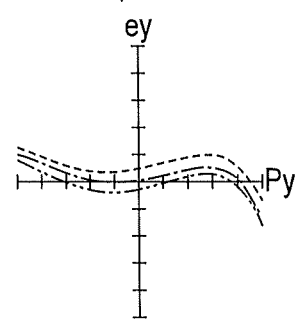 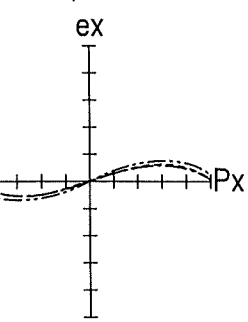
FIG.13G Ta,IH 0.7
FIG.13H Sa,IH 0.7
FIG.13I Ta,IH 1.0
FIG.13J Sa,IH 1.0

FIG.14A
AS
FIY 0.94
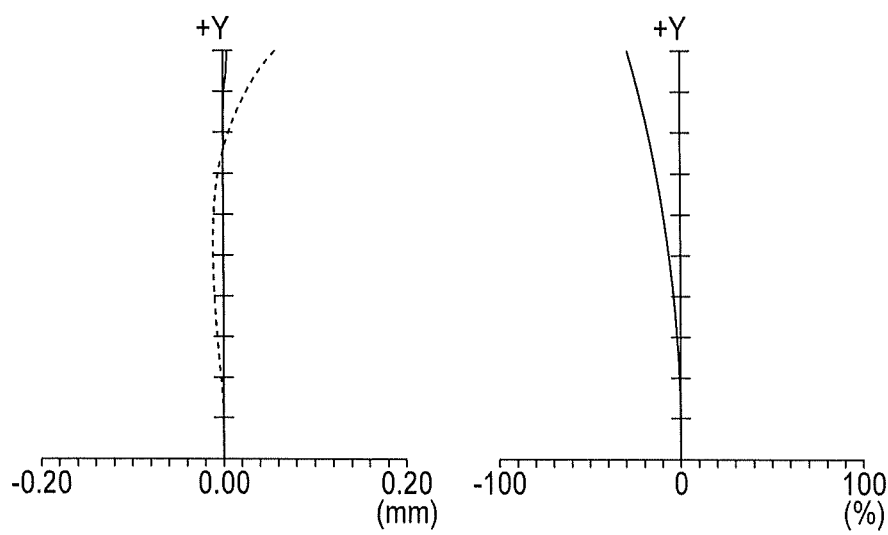
FIG.14B
DT
FIY 0.94
FIG.14C
Ta,IH 0
ey
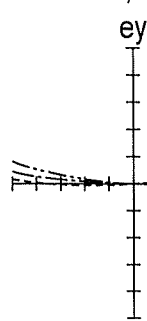
FIG.14D
Sa,IH 0
ex
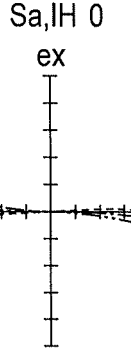
FIG.14E
Ta,IH 0.5
ey
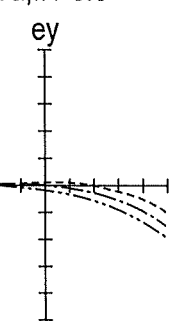
FIG.14F
Sa,IH 0.5
ex
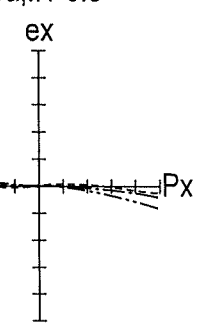
FIG.14G
Ta,IH 0.7
ey
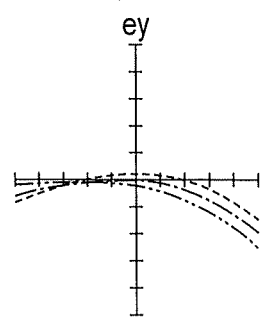
FIG.14H
Sa,IH 0.7
ex
FIG.14I
Ta,IH 1.0
ey
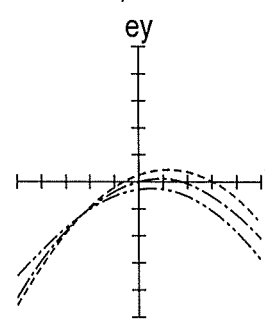
FIG.14J
Sa,IH 1.0
ex
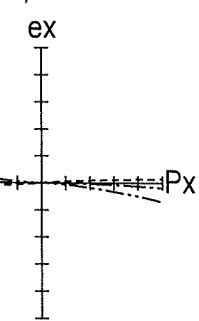

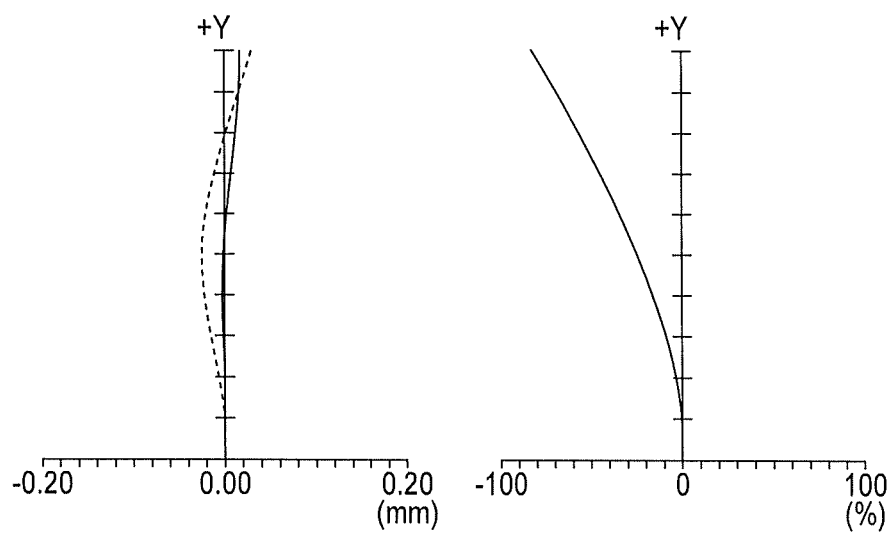

AS
FIY 0.90

DT
FIY 0.90

Ta,IH 0
ey

Sa,IH 0
ex

Ta,IH 0.5
ey

Sa,IH 0.5
ex

Ta,IH 0.7
ey

Sa,IH 0.7
ex

Ta,IH 1.0
ey

Sa,IH 1.0
ex

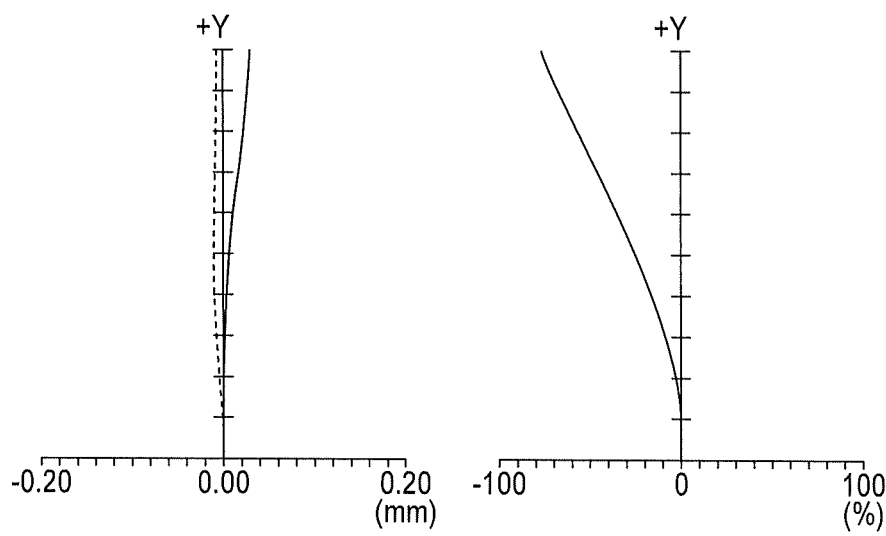
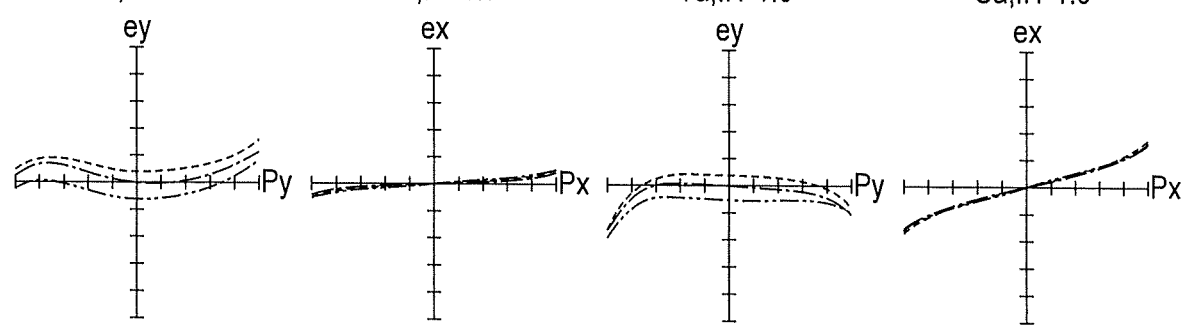

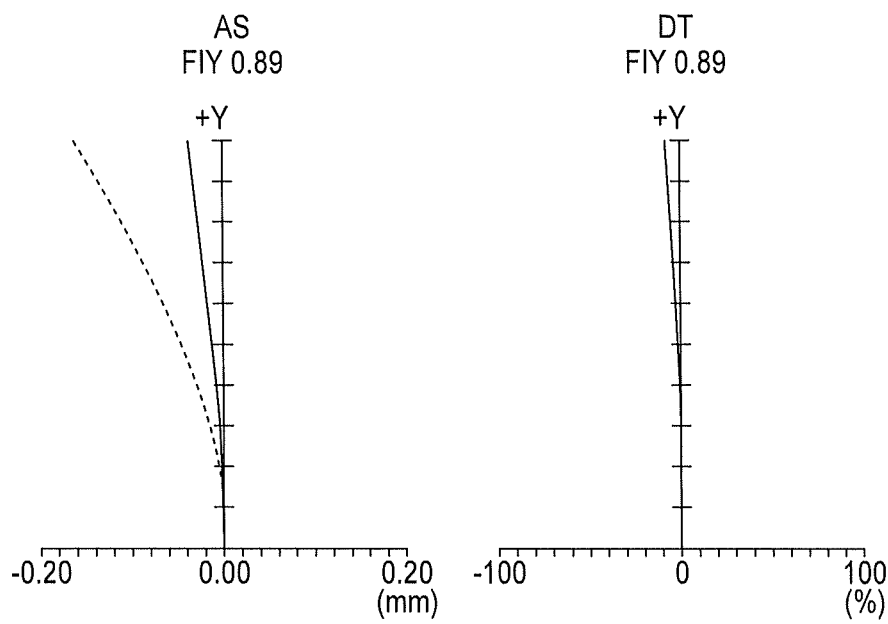
FIG.18A
AS
FIY 0.89
FIG.18B
DT
FIY 0.89
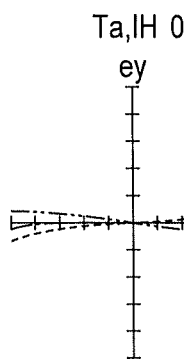
FIG.18C
Ta,IH 0
ey
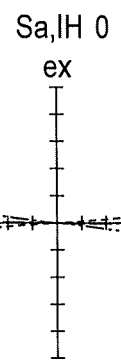
FIG.18D
Sa,IH 0
ex
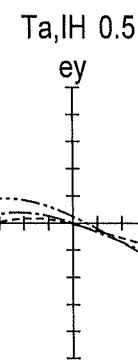
FIG.18E
Ta,IH 0.5
ey
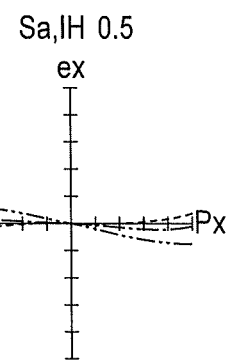
FIG.18F
Sa,IH 0.5
ex
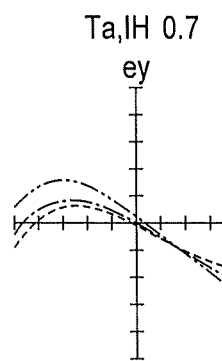
FIG.18G
Ta,IH 0.7
ey
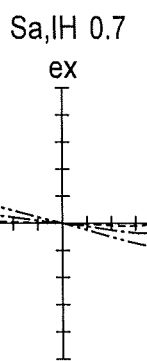
FIG.18H
Sa,IH 0.7
ex
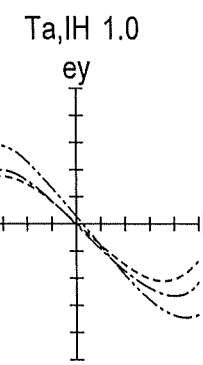
FIG.18I
Ta,IH 1.0
ey
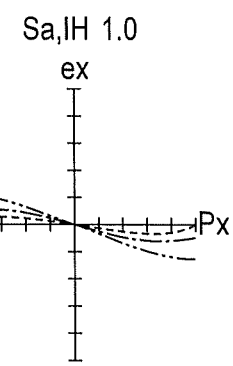
FIG.18J
Sa,IH 1.0
ex

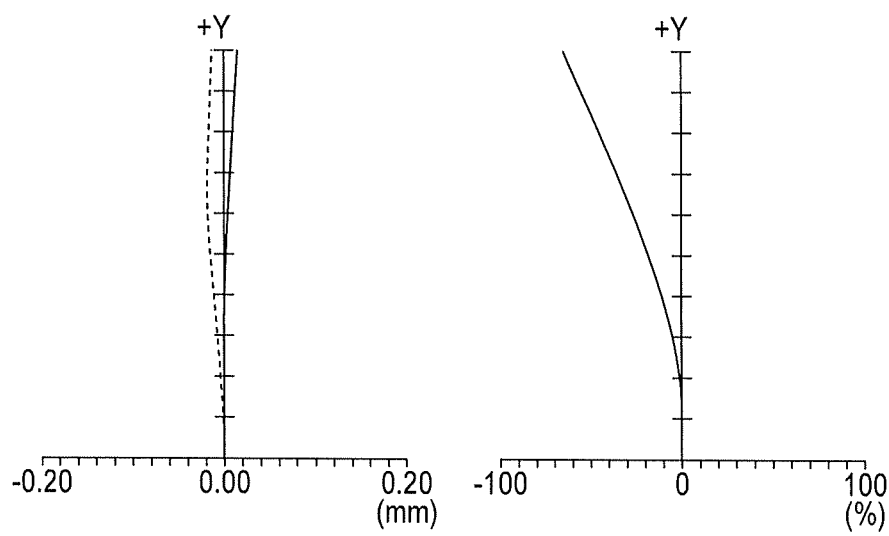
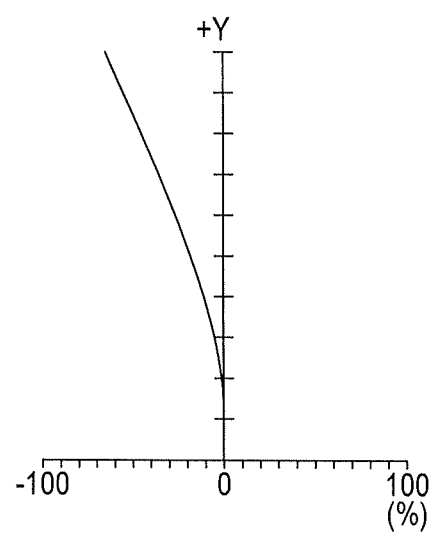
FIG.19A AS FIY 0.89
FIG.19B DT FIY 0.89
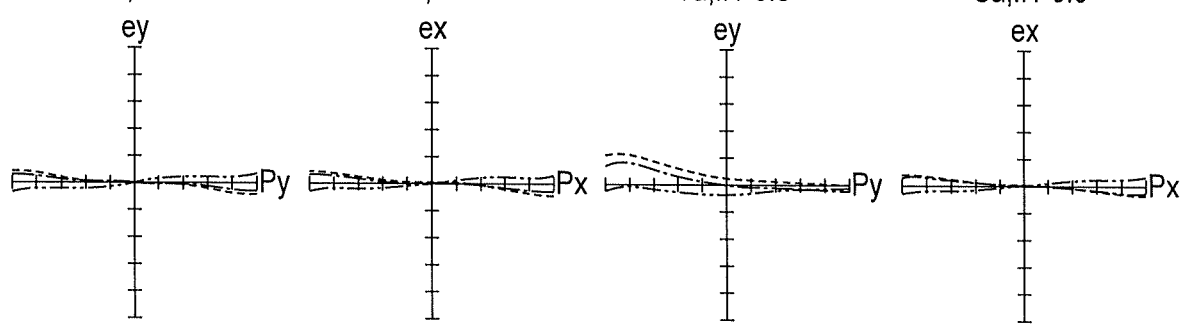
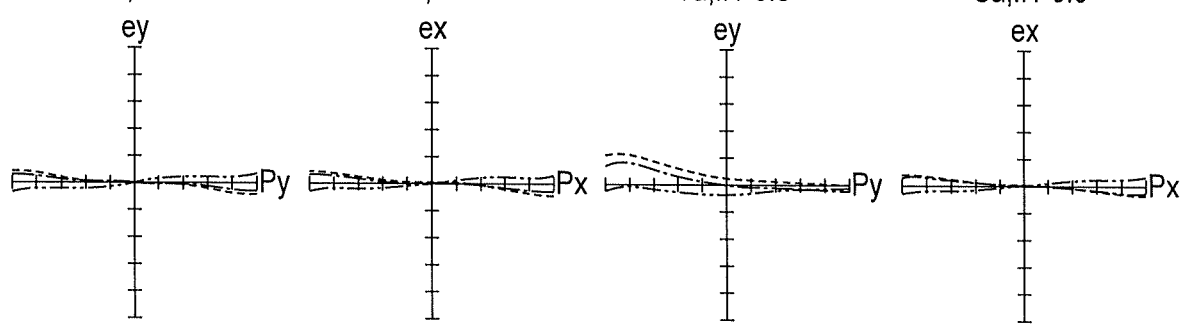
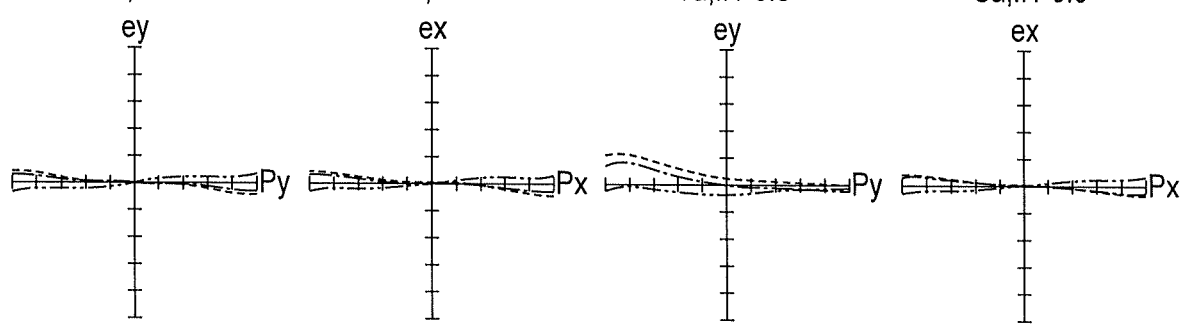
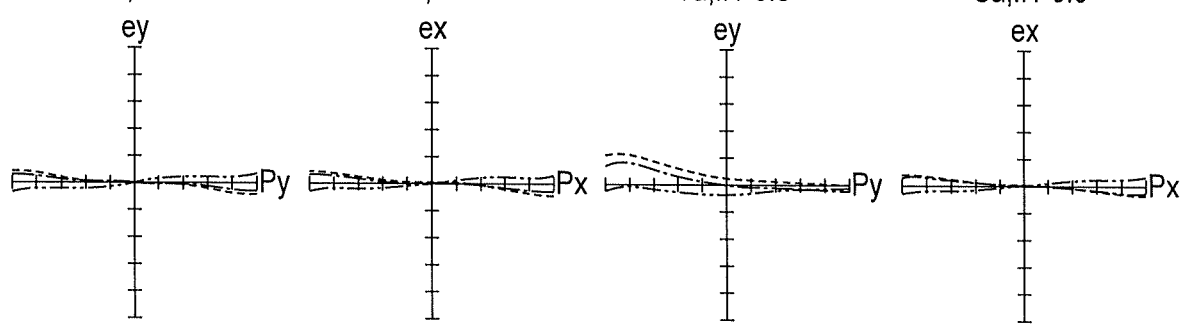
FIG.19C Ta,IH 0  
FIG.19D Sa,IH 0  
FIG.19E Ta,IH 0.5  
FIG.19F Sa,IH 0.5
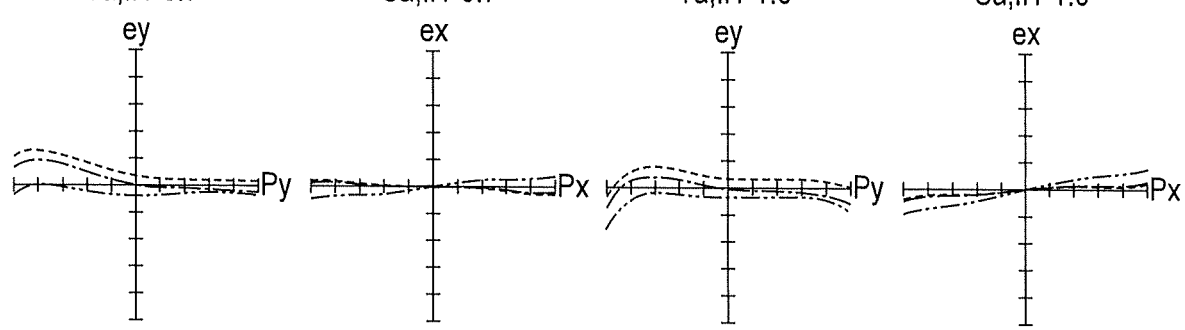
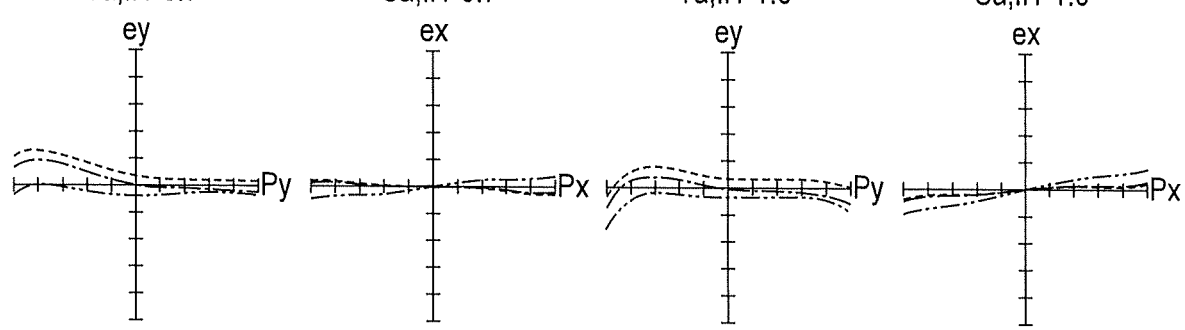
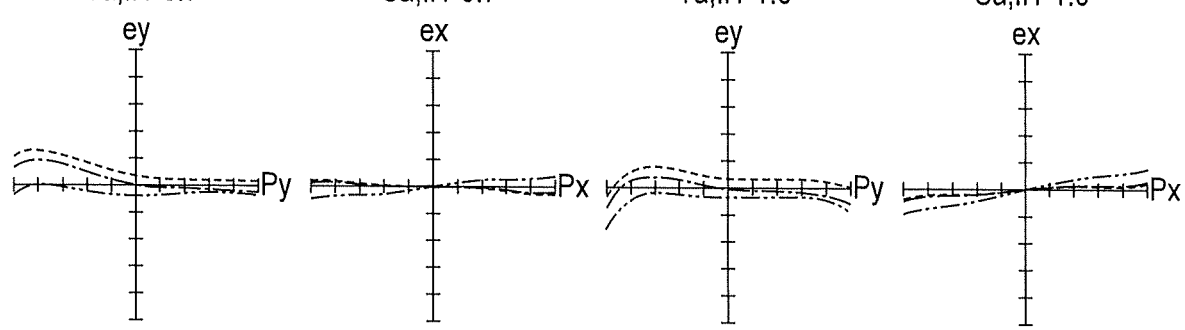
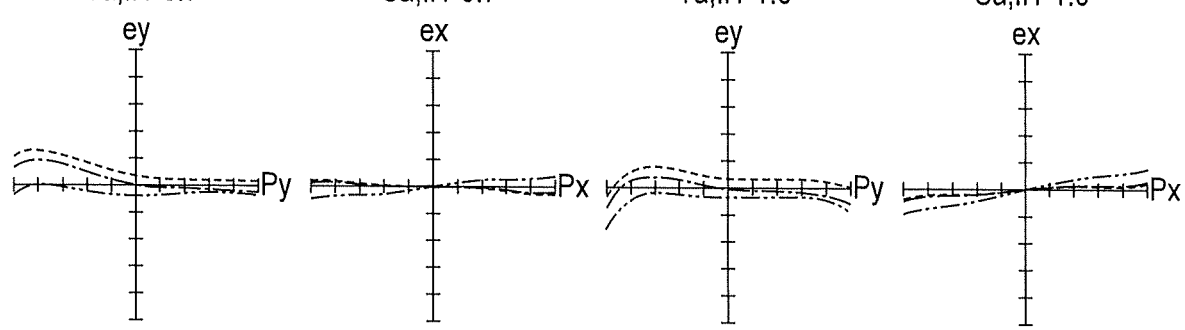
FIG.19G Ta,IH 0.7  
FIG.19H Sa,IH 0.7  
FIG.19I Ta,IH 1.0  
FIG.19J Sa,IH 1.0

AS
FIY 0.78

DT
FIY 0.78

Ta,IH 0
ey

Sa,IH 0
ex

Ta,IH 0.5
ey

Sa,IH 0.5
ex

Ta,IH 0.7
ey

Sa,IH 0.7
ex

Ta,IH 1.0
ey

Sa,IH 1.0
ex

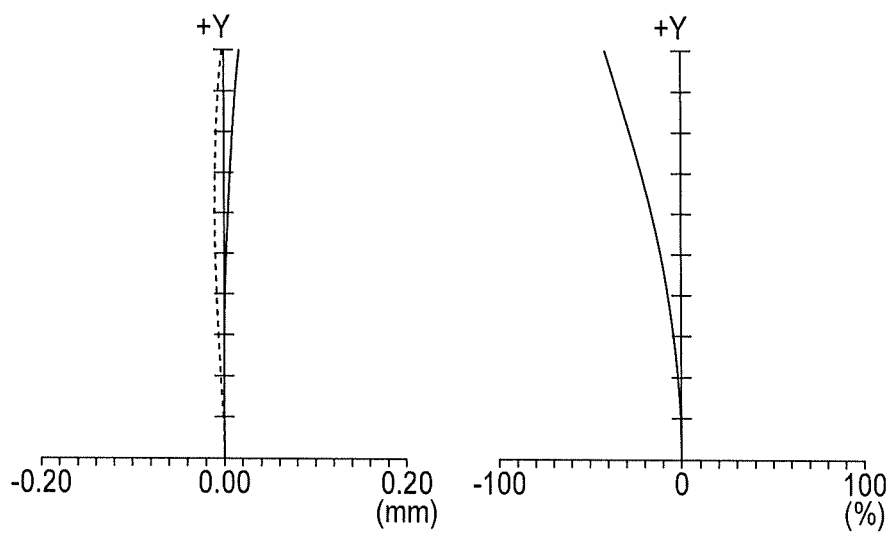
FIG.21A
AS
FIY 0.78
FIG.21B
DT
FIY 0.78
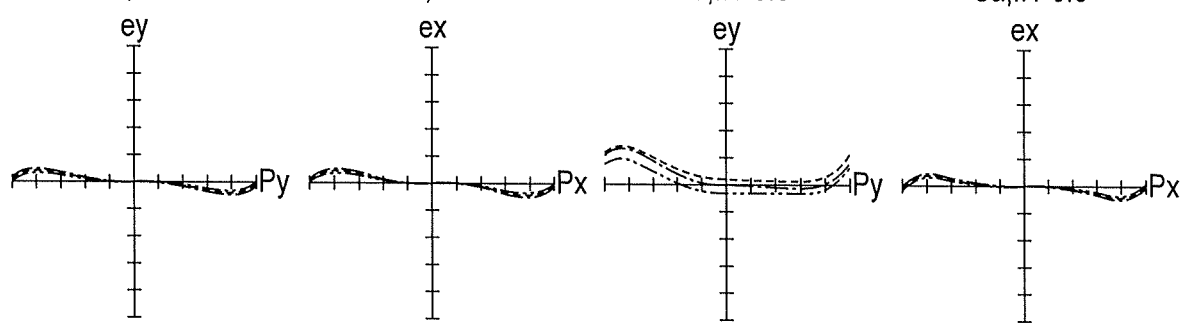
FIG.21C Ta,IH 0
FIG.21D Sa,IH 0
FIG.21E Ta,IH 0.5
FIG.21F Sa,IH 0.5
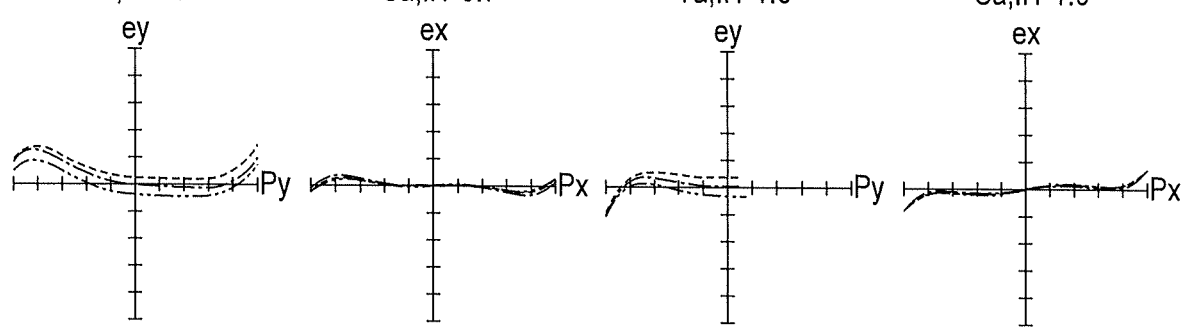
FIG.21G Ta,IH 0.7
FIG.21H Sa,IH 0.7
FIG.21I Ta,IH 1.0
FIG.21J Sa,IH 1.0

AS
FIY 0.89

DT
FIY 0.89

Ta,IH 0
ey

Sa,IH 0
ex

Ta,IH 0.5
ey

Sa,IH 0.5
ex

Ta,IH 0.7
ey

Sa,IH 0.7
ex

Ta,IH 1.0
ey

Sa,IH 1.0
ex

FIG23A
AS
FIY 0.89
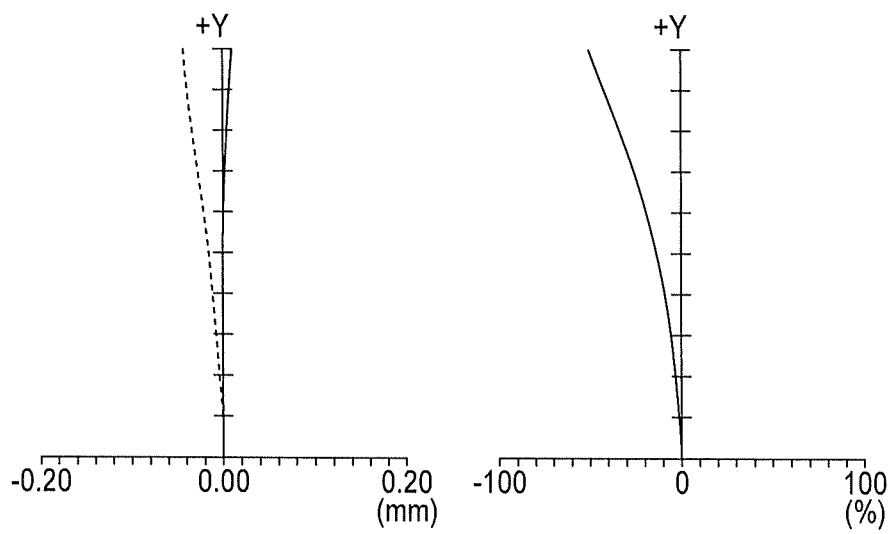
FIG23B
DT
FIY 0.89
FIG.23C
Ta,IH 0
ey
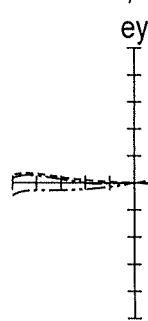
FIG.23D
Sa,IH 0
ex
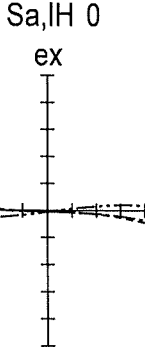
FIG.23E
Ta,IH 0.5
ey
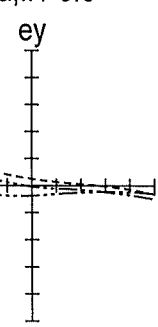
FIG.23F
Sa,IH 0.5
ex
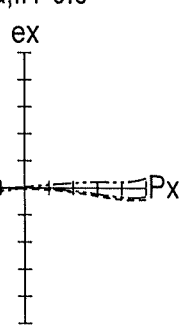
FIG.23G
Ta,IH 0.7
ey
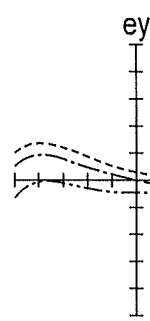
FIG.23H
Sa,IH 0.7
ex
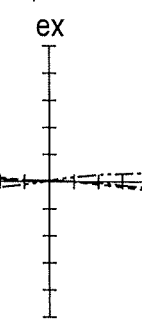
FIG.23I
Ta,IH 1.0
ey
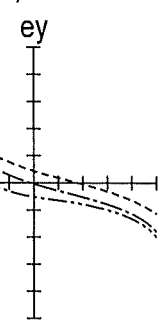
FIG.23J
Sa,IH 1.0
ex
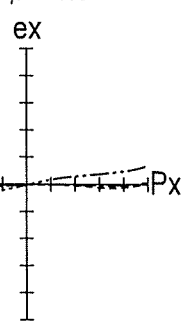

OPTICAL SYSTEM FOR STEREOSCOPIC VISION AND IMAGE PICKUP APPARATUS USING THE SAME

CROSS-REFERENCE TO RELATED APPLICATION

The present application is a continuation application of International Application No. PCT/JP2017/024301 filed on Jul. 3, 2017, the entire contents of which are incorporated herein by reference.

BACKGROUND

Technical Field

The present disclosure relates to an optical system for stereoscopic vision and an image pickup apparatus using the same, and mainly to an optical system for stereoscopic vision which is used in a field of endoscopes, and an image pickup apparatus using the same.

Description of the Related Art

As a pupil distance varies for the same object point, an angle of convergence varies. As the angle of convergence varies, a stereoscopic vision (hereinafter, referred to as 'stereoscopic effect') varies. The angle of convergence is an angle made by a line of sight of a right eye and a line of sight of a left eye when the same object point is viewed.

An image pickup apparatus which generates an image that can carry out stereoscopic vision is known. In this apparatus, an image for left eye and an image for the right eye are acquired.

In Japanese Patent Application Laid-open Publication No. 2012-113281, an apparatus which includes a pair of optical systems is disclosed. The pair of optical systems is arranged in parallel. A stop having an opening section is disposed in each optical system.

When the pair of optical systems is deemed as two eyes of a human being, a distance between the two opening sections, or in other words, a distance between the two stops is corresponds to a distance between pupils.

In the apparatus in Japanese Patent Application Laid-open Publication No. 2012-113281, light emerged from the same object point is incident on the pair of optical systems. Out of the incident light, a light ray passing through a center of the opening section corresponds to the line of sight. A light ray passing through the center of the opening section of one optical system and a light ray passing through the center of the opening section of the other optical system intersect at a position of the same object point. When an angle of intersection of these two lines of intersection is an inward angle, the inward angle corresponds to the angle of convergence.

In the apparatus in Japanese Patent Application Laid-open Publication No. 2012-113281, it is possible to vary the distance between the two stops. By varying the distance between the two stops, the inward angle varies. As a result, it is possible to vary the stereoscopic effect.

SUMMARY

An optical system for stereoscopic vision according to at least some embodiments of the present disclosure includes:
a first optical system, and
a second optical system, wherein
each of the first optical system and the second optical system includes a stop and a plurality of lens units,
the plurality of lens units includes at least one movable lens unit which moves at the time of focusing,
at least focusing to a near point and focusing to a far point is carried out by a movement of the movable lens unit, and
at the time of focusing to the near point, both a first entrance pupil and a second entrance pupil are positioned on an image side of positions at the time of focusing to the far point, and here,
the first entrance pupil is an entrance pupil of the first optical system,
the second entrance pupil is an entrance pupil of the second optical system,
the near point is a point in a focusing range, positioned nearest to the optical system for stereoscopic vision, and
the far point is a point in the focusing range, positioned farthest from the optical system for stereoscopic vision.

Moreover, another optical system for stereoscopic vision according to at least some embodiments of the present disclosure includes:
a first optical system,
a second optical system, and
an optical element, wherein
the first optical system and the second optical system are disposed on an image side of the optical element,
the optical element is positioned to intersect both an optical axis of the first optical system and an optical axis of the second optical system,
each of the first optical system and the second optical system includes a stop and at least two movable lens units which move at the time of focusing,
the two movable lens units include in order from the object side, a first movable lens unit and a second movable lens unit,
at least focusing to a near point and focusing to a far point is carried out by the movement of at least the second movable lens unit,
at the time of focusing from the far point to the near point, the first movable lens unit moves from the object side toward the image side, and
the following conditional expression (1) is satisfied:

$$-0.1 < FL1m/FLc < 0.1 \tag{1}$$

where,
FLc denotes a focal length of the optical element,
FL1m denotes a focal length of the first movable lens unit in the first optical system and a focal length of the first movable lens unit in the second optical system,
the near point is a point in a focusing range, positioned nearest to the optical system for stereoscopic vision, and
the far point is a point in the focusing range, positioned farthest from the optical system for stereoscopic vision.

Furthermore, another optical system for stereoscopic vision according to at least some embodiments of the present disclosure includes:
a first optical system, and
a second optical system, wherein
each of the first optical system and the second optical system includes a stop and a movable lens unit which moves at the time of focusing,
at least focusing to a near point and focusing to a far point is carried out by a movement of the movable lens unit, and
a focus position is changed by moving the movable lens unit while making satisfy the following conditional expression (2):

$$0.1 < a\,\tan(De/Loben) - a\,\tan(De/Lobef) < 0.8 \tag{2}$$

where,

De denotes a distance between a center of a first entrance pupil and a center of a second entrance pupil, Loben denotes a distance on an optical axis from a position of the near point up to a position of the first entrance pupil at the time of focusing to the near point and a distance on the optical axis from the position of the near point up to a position of the second entrance pupil at the time of focusing to the near point, and Lobef denotes a distance on the optical axis from a position of the far point up to a position of the first entrance pupil at the time of focusing to the far point and a distance on the optical axis from the position of the far point up to a position of the second entrance pupil at the time of focusing to the far point, and here the first entrance pupil is an entrance pupil of the first optical system, the second entrance pupil is an entrance pupil of the second optical system, the near point is a point in a focusing range, positioned nearest to the optical system for stereoscopic vision, and the far point is a point in the focusing range, positioned farthest from the optical system for stereoscopic vision.

Another optical system for stereoscopic vision according to at least some aspects of the present disclosure includes:

a first optical system, a second optical system, and an optical element, wherein the first optical system and the second optical system are disposed on an image side of the optical element, each of the first optical system and the second optical system includes a stop and a lens unit having a negative refractive power, at the time of focusing from a far point to a near point, the optical element is fixed, and the lens unit having a negative refractive power moves from the object side toward the image side as a movable lens unit, and the following conditional expression (3) is satisfied:

$$5.0<(Lnobf-Lnobn)/Dax<50.0 \quad (3)$$

where,

Dax denotes a distance between an optical axis of the first optical system and an optical axis of the second optical system, Lnobf denotes a distance on an optical axis from a surface nearest to an object of the lens unit having a negative refractive power in the first optical system at the time of focusing to the far point up to a position of the far point, and a distance on the optical axis from a surface nearest to the object of the lens unit having a negative refractive power in the second optical system at the time of focusing to the far point up to the position of the far point, and Lnobn denotes a distance on the optical axis from the surface nearest to the object of the lens unit having a negative refractive power in the first optical system at the time of focusing to the near point up to a position of the near point, and a distance on the optical axis from the surface nearest to the object of the lens unit having a negative refractive power in the second optical system at the time of focusing to the near point up to the position of the near point, and here the near point is a point in a focusing range, positioned nearest to the optical system for stereoscopic vision, and the far point is a point in the focusing range, positioned farthest from the optical system for stereoscopic vision.

An image pickup apparatus according to at least some embodiments of the present disclosure includes:

an optical system, and an imager which has an image pickup surface, and which converts an image formed on the image pickup surface by the optical system to an electric signal, wherein the optical system is the abovementioned optical system for stereoscopic vision.

BRIEF DESCRIPTION OF THE DRAWINGS

FIG. 13A, FIG. 13B, FIG. 13C, FIG. 13D, FIG. 13E, FIG. 13F, FIG. 13G, FIG. 13H, FIG. 13I, and FIG. 13J are aberration diagrams of the optical system for stereoscopic vision of the example 1;

FIG. 14A, FIG. 14B, FIG. 14C, FIG. 14D, FIG. 14E, FIG. 14F, FIG. 14G, FIG. 14H, FIG. 14I, and FIG. 14J are aberration diagrams of the optical system for stereoscopic vision of the example 2;

FIG. 15A, FIG. 15B, FIG. 15C, FIG. 15D, FIG. 15E, FIG. 15F, FIG. 15G, FIG. 15H, FIG. 15I, and FIG. 15J are aberration diagrams of the optical system for stereoscopic vision of the example 2;

FIG. 17A, FIG. 17B, FIG. 17C, FIG. 17D, FIG. 17E, FIG. 17F, FIG. 17G, FIG. 17H, FIG. 17I, and FIG. 17J are aberration diagrams of the optical system for stereoscopic vision of the example 3;

FIG. 18A, FIG. 18B, FIG. 18C, FIG. 18D, FIG. 18E, FIG. 18F, FIG. 18G, FIG. 18H, FIG. 18I, and FIG. 18J are aberration diagrams of the optical system for stereoscopic vision of the example 4;

FIG. 19A, FIG. 19B, FIG. 19C, FIG. 19D, FIG. 19E, FIG. 19F, FIG. 19G, FIG. 19H, FIG. 19I, and FIG. 19J are aberration diagrams of the optical system for stereoscopic vision of the example 4;

FIG. 21A, FIG. 21B, FIG. 21C, FIG. 21D, FIG. 21E, FIG. 21F, FIG. 21G, FIG. 21H, FIG. 21I, and FIG. 21J are aberration diagrams of the optical system for stereoscopic vision of the example 5;

FIG. 23A, FIG. 23B, FIG. 23C, FIG. 23D, FIG. 23E, FIG. 23F, FIG. 23G, FIG. 23H, FIG. 23I, and FIG. 23J are aberration diagrams of the optical system for stereoscopic vision of the example 6.

DETAILED DESCRIPTION

Figure 1A:
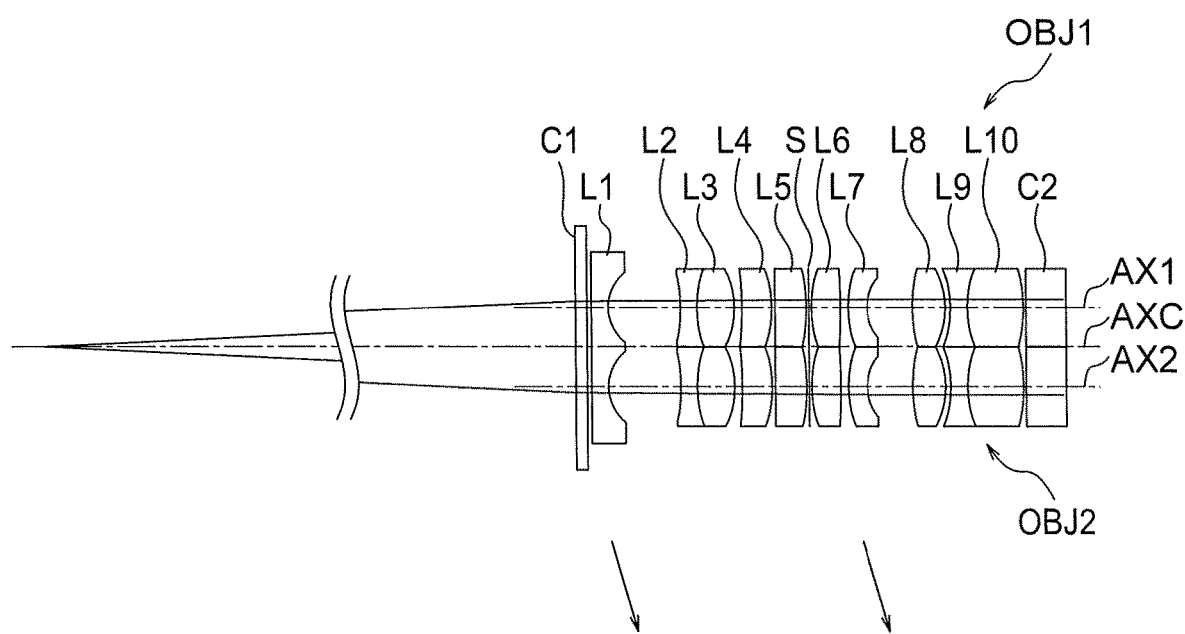
FIG. 1A and FIG. 1B are lens cross-sectional views of a common optical system.

Action and effect of embodiments according to certain aspects of the present disclosure will be described below. In the explanation of the action and effect of the embodiments concretely, the explanation will be made by citing concrete examples. However, similar to a case of the examples to be described later, aspects exemplified thereof are only some of the aspects included in the present disclosure, and there exists a large number of variations in these aspects. Consequently, the present disclosure is not restricted to the aspects that will be exemplified.

Optical systems for stereoscopic vision from an optical system for stereoscopic vision of a first embodiment to an optical system for stereoscopic vision of a fourth embodiment will be described below. Prior to the description, an optical system which is common to the optical systems for stereoscopic vision of the four embodiments (hereinafter, referred to as 'common optical system') will be described below.

The common optical system includes a first optical system and a second optical system. The first optical system and the second optical system are disposed in parallel with a central axis interposed between the two optical systems. An optical axis of the first optical system, an optical axis of the second optical system, and the central axis are positioned on a same plane.

Two images are formed by the first optical system and the second optical system respectively. As mentioned above, the first optical system and the second optical system are disposed in parallel. Therefore, a shift occurs between an image formed by the first optical system and an image formed by the second optical system. This shift occurs in a direction parallel to the abovementioned same plane and orthogonal to the central axis (hereinafter, referred to as 'parallax direction'). Therefore, by using these two images, it is possible to carry out stereoscopic vision.

The central axis is an axis positioned between the optical axis of the first optical system and the optical axis of the second optical system. The first optical system and the second optical system are disposed such that a distance from the central axis up to the optical axis of the first optical system and a distance from the central axis up to the optical axis of the second optical system become equal.

As mentioned above, in the common optical system, the first optical system and the second optical system are disposed in parallel. Moreover, each of the first optical system and the second optical system includes the stop. In the stop, an opening section is provided. When the first optical system and the second optical system are deemed as human eyes, a distance between the two opening sections, or in other words, a distance between the two stops corresponds to a distance between pupils.

An angle of convergence is an angle made by a line of sight of a right eye and a line of sight of a left eye when the same object point is viewed. In the common optical system, light emerged from the same object point is incident on the first optical system and the second optical system. Out of the incident light, a light ray passing through a center of the opening section corresponds to the line of sight. A light ray passing through a center of the opening section of the first optical system and a light ray passing through a center of the opening section of the second optical system intersect at a position of the same object point. When an angle made by these two intersecting light rays is an inward angle, the inward angle corresponds to the angle of convergence.

As a pupil distance varies for the same object point, the angle of convergence varies. As the angle of convergence varies, a stereoscopic vision (hereinafter, referred to as 'stereoscopic effect') varies. Accordingly, the inward angle varies by moving of the two stops to be drawn away from the central axis or by the moving of the two stops to come closer to the central axis. As a result, it is possible to vary the stereoscopic effect.

Figure 1B:
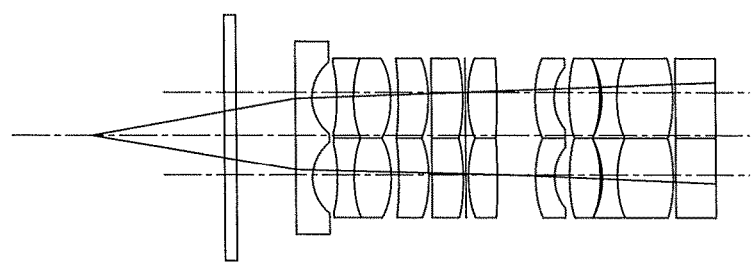
Figure 2:
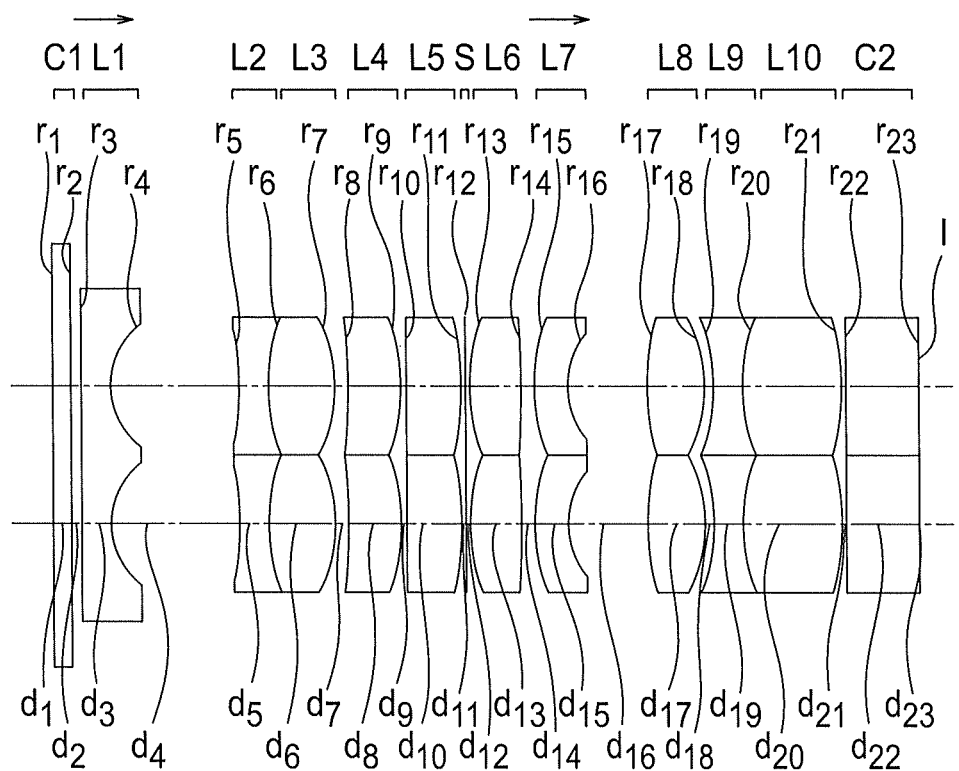
FIG. 2 is a lens cross-sectional view of an optical system for stereoscopic vision of an example 1.
Figure 3:
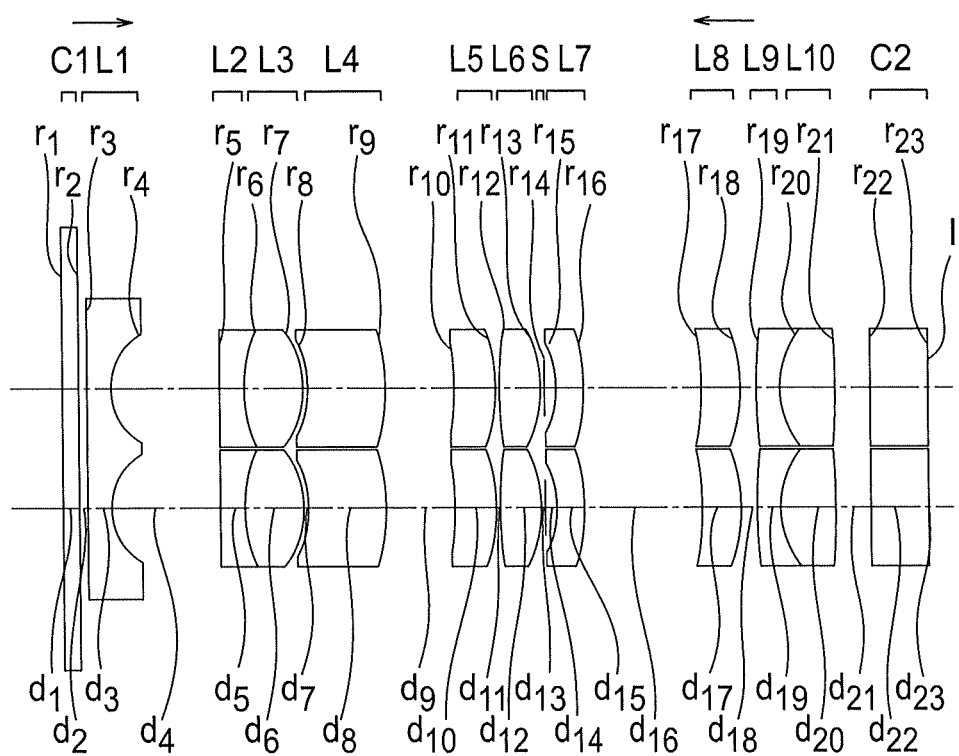
FIG. 3 is a lens cross-sectional view of an optical system for stereoscopic vision of an example 2.
Figure 4:
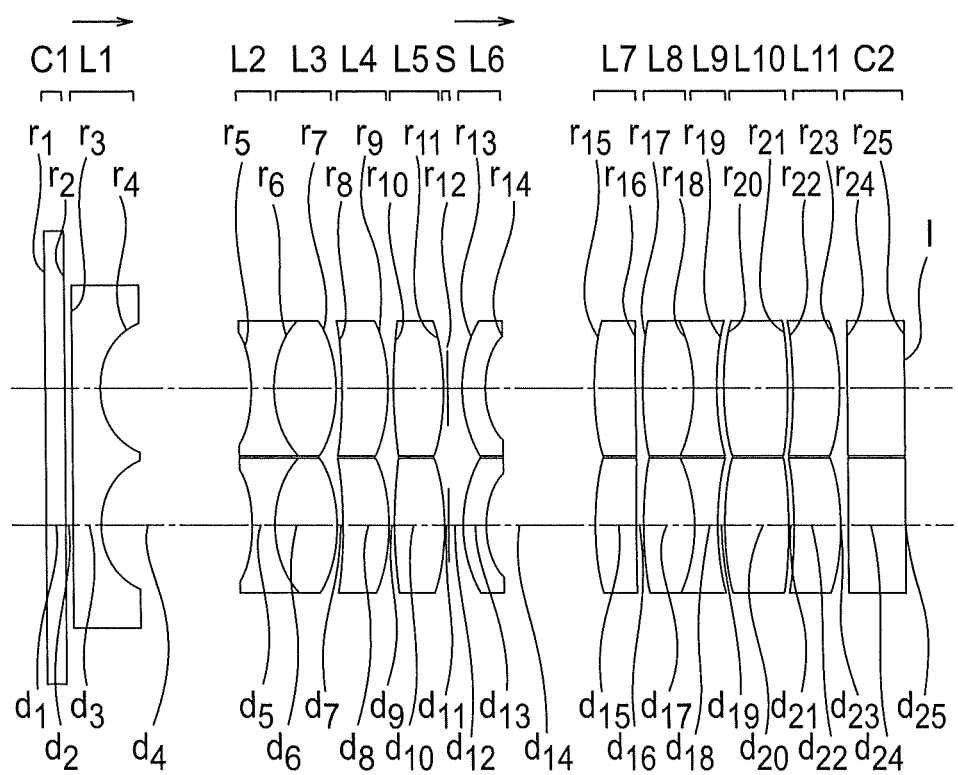
FIG. 4 is a lens cross-sectional view of an optical system for stereoscopic vision of an example 3.
Figure 5:
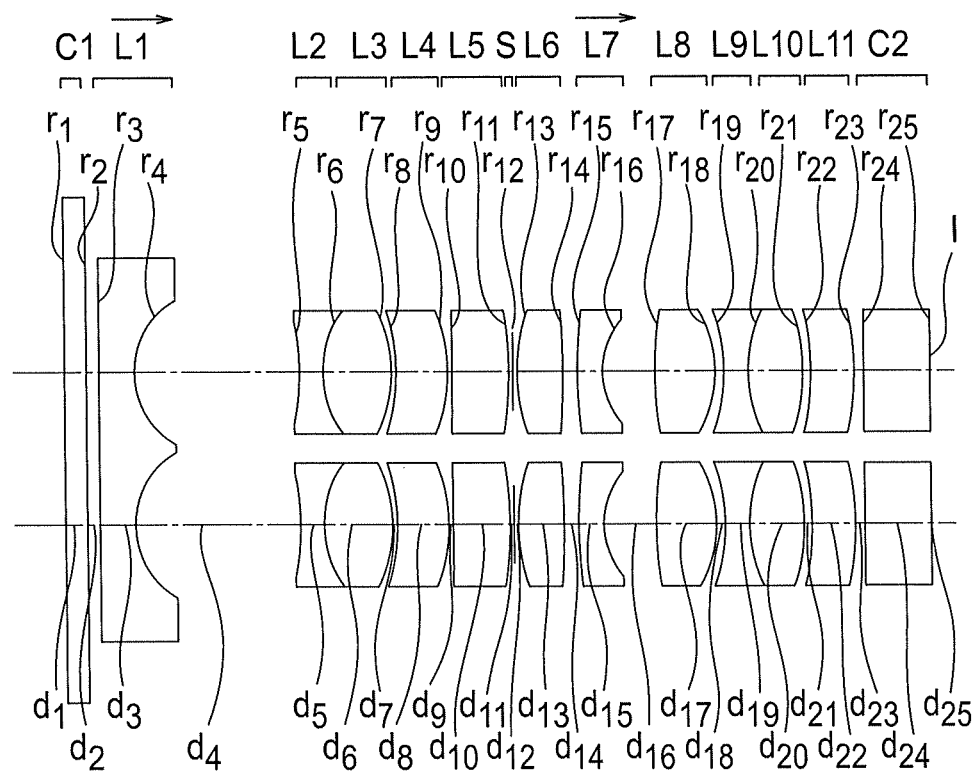
FIG. 5 is a lens cross-sectional view of an optical system for stereoscopic vision of an example 4.
Figure 6:
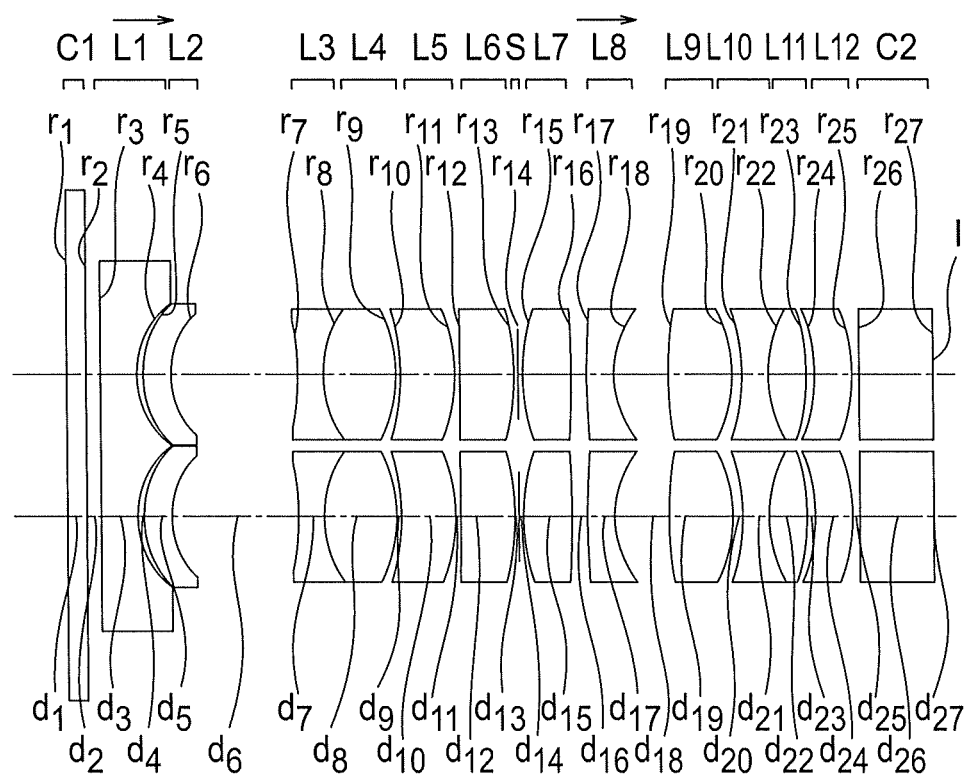
FIG. 6 is a lens cross-sectional view of an optical system for stereoscopic vision of an example 5.
Figure 7:
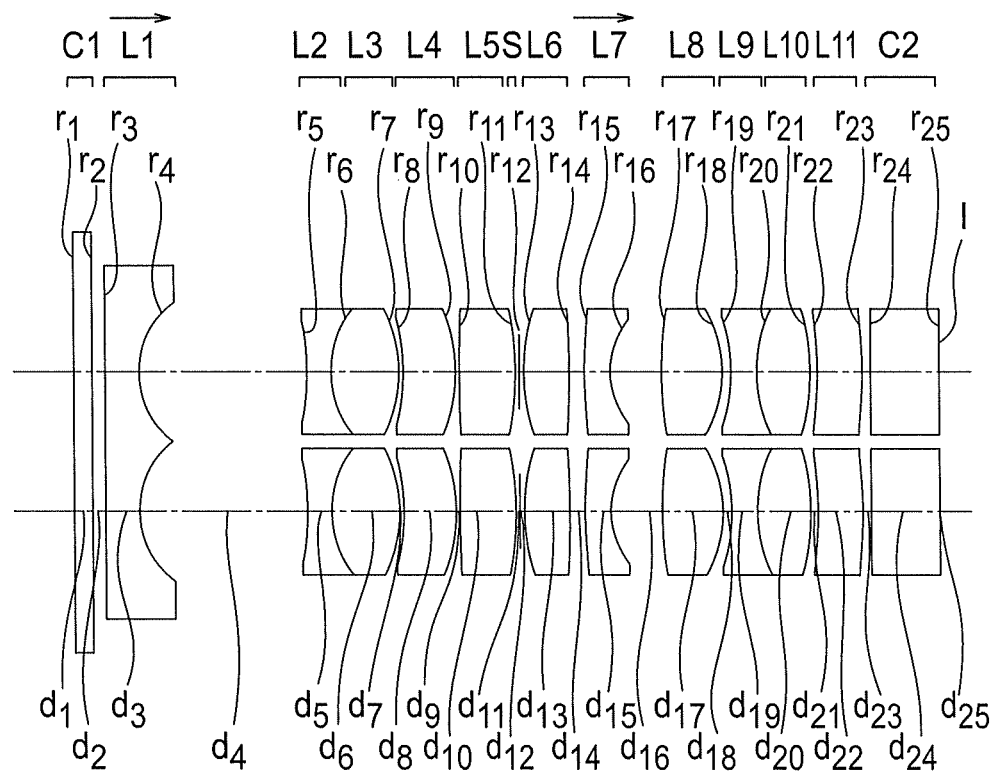
FIG. 7 is a lens cross-sectional view of an optical system for stereoscopic vision of an example 6.
Figure 8:
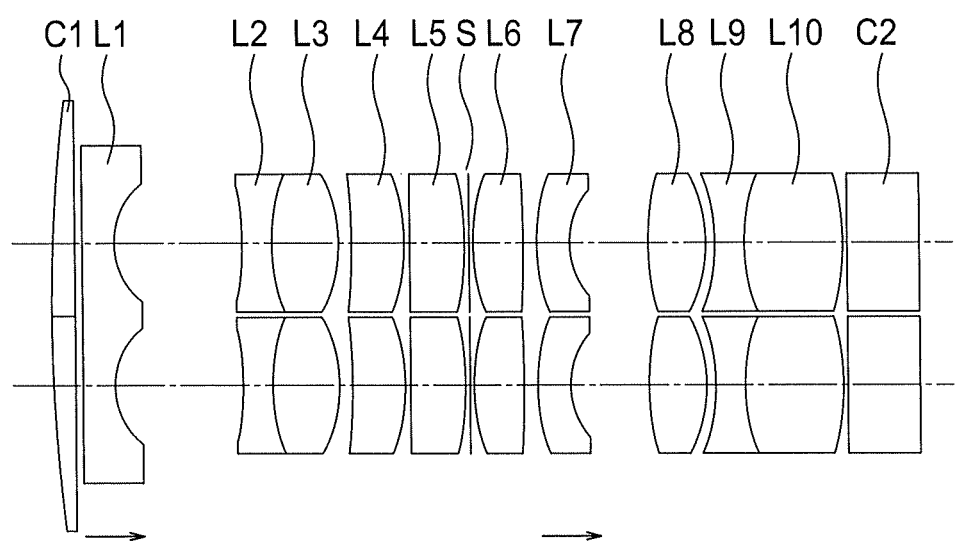
FIG. 8 is a lens cross-sectional view of an optical system for stereoscopic vision of a modified example 1.
Figure 9:
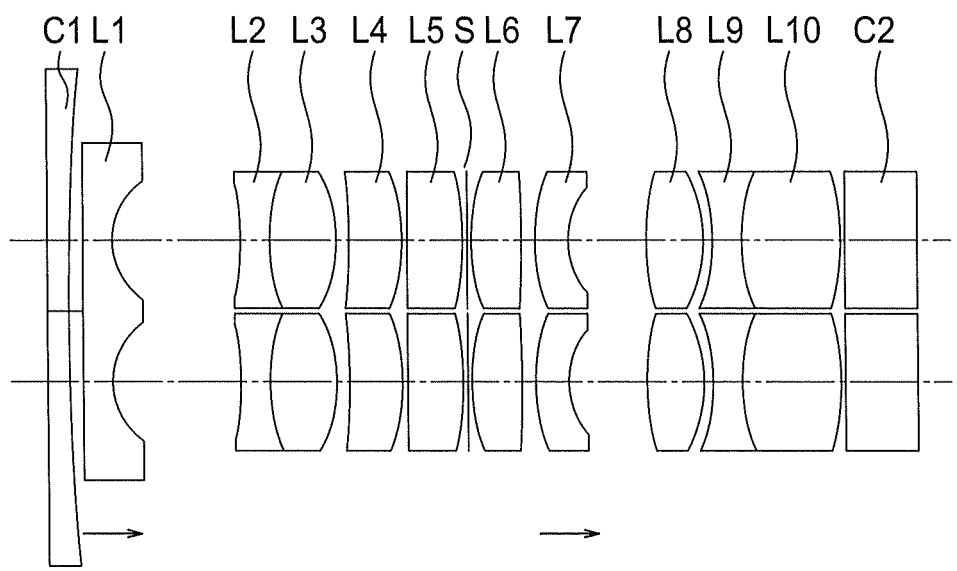
FIG. 9 is a lens cross-sectional view of an optical system for stereoscopic vision of a modified example 2.
Figure 10:
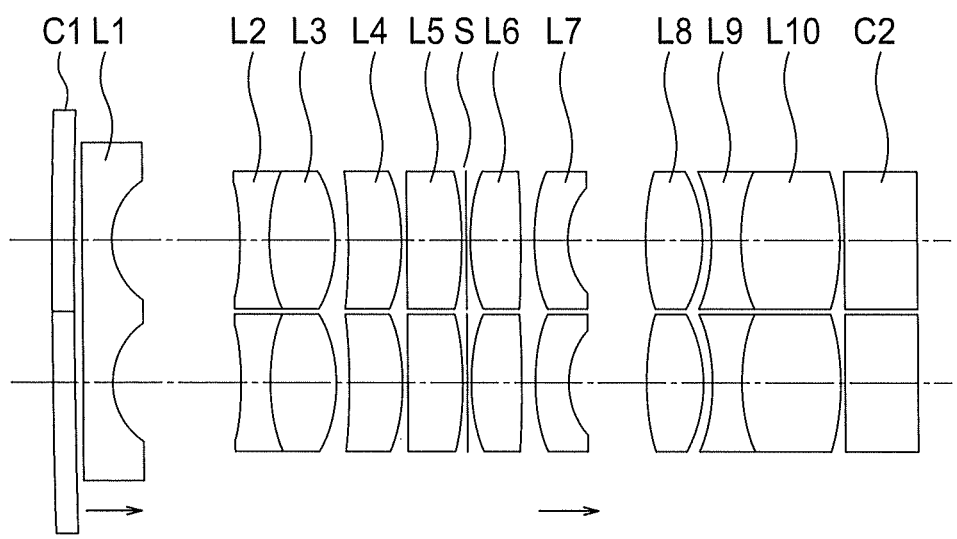
FIG. 10 is a lens cross-sectional view of an optical system for stereoscopic vision of a modified example 3.
Figure 11:
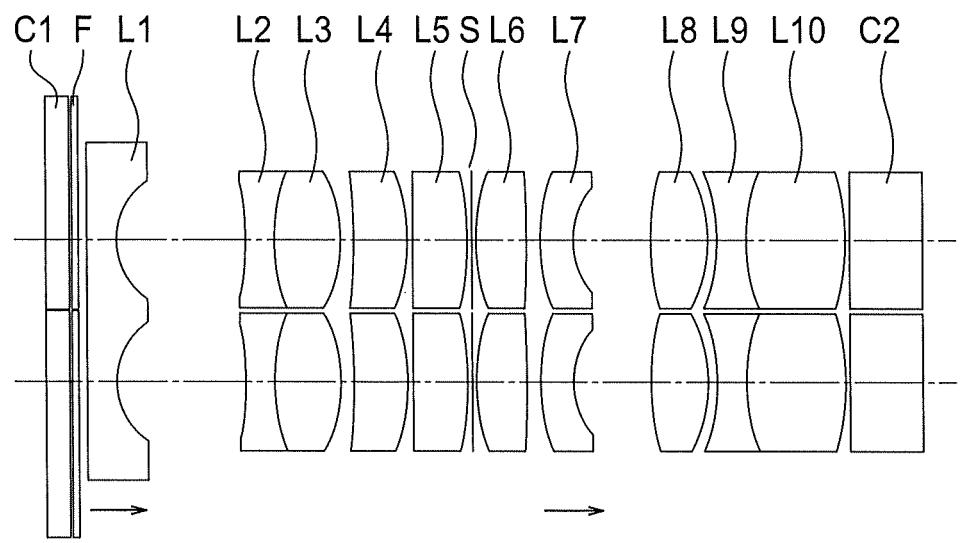
FIG. 11 is a lens cross-sectional view of an optical system for stereoscopic vision of a modified example 4.
Figure 12A:
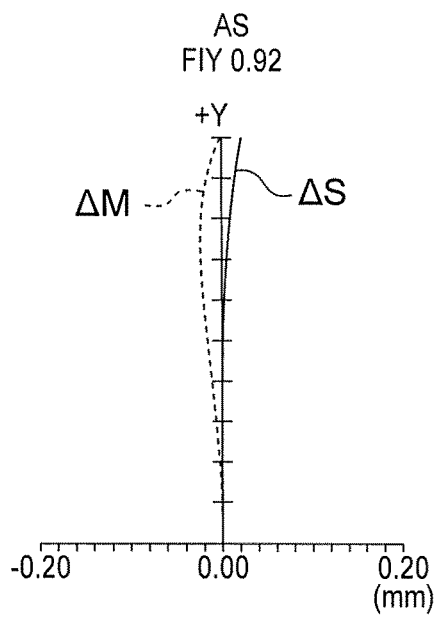
FIG. 12A, FIG. 12B, FIG. 12C, FIG. 12D, FIG. 12E, FIG. 12F, FIG. 12G, FIG. 12H, FIG. 12I, and FIG. 12J are aberration diagrams of the optical system for stereoscopic vision of the example 1.
Figure 12B:
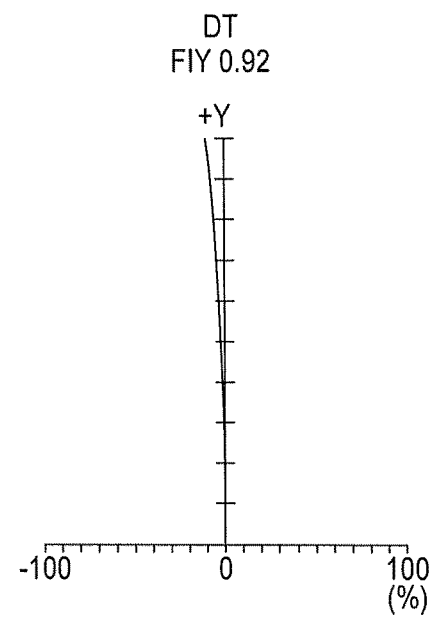
Figure 12C:
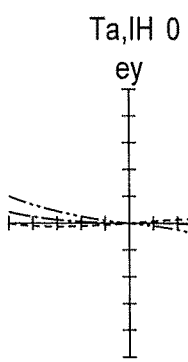
Figure 12D:
Figure 12E:
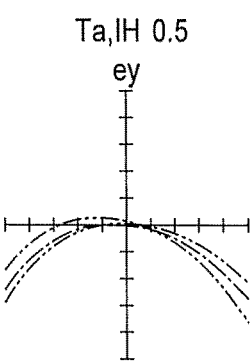
Figure 12F:
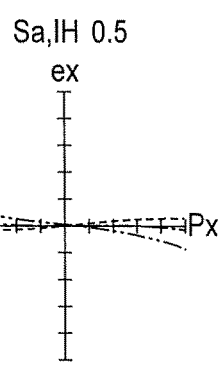
Figure 12G:
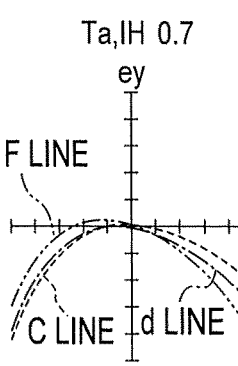
Figure 12H:
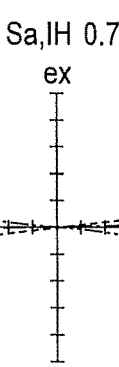
Figure 12I:
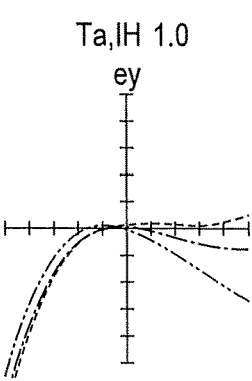
Figure 12J:
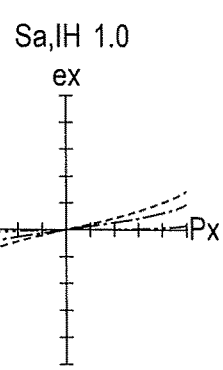
Figure 16A:
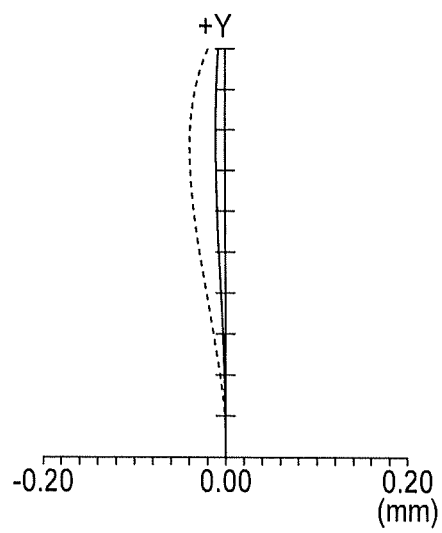
FIG. 16A, FIG. 16B, FIG. 16C, FIG. 16D, FIG. 16E, FIG. 16F, FIG. 16G, FIG. 16H, FIG. 16I, and FIG. 16J are aberration diagrams of the optical system for stereoscopic vision of the example 3.
Figure 16B:
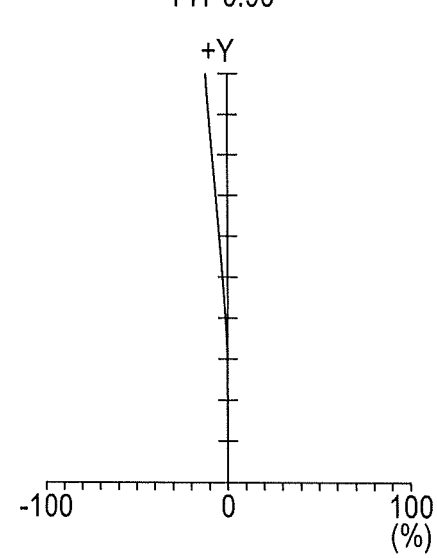
Figure 16C:
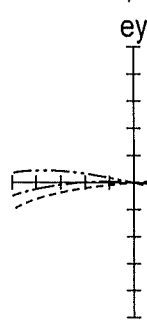
Figure 16D:
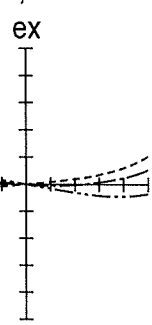
Figure 16E:
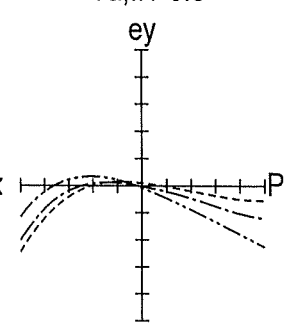
Figure 16F:
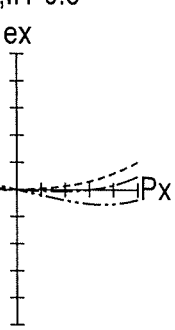
Figure 16G:
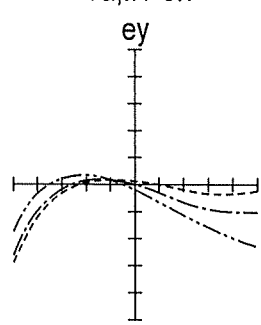
Figure 16H:
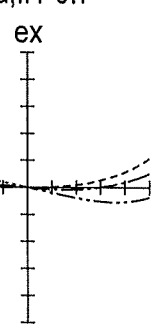
Figure 16I:
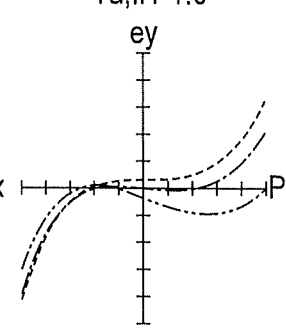
Figure 16J:
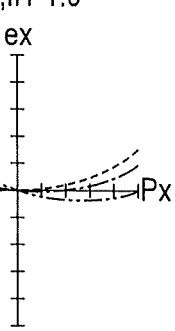
Figure 20A:
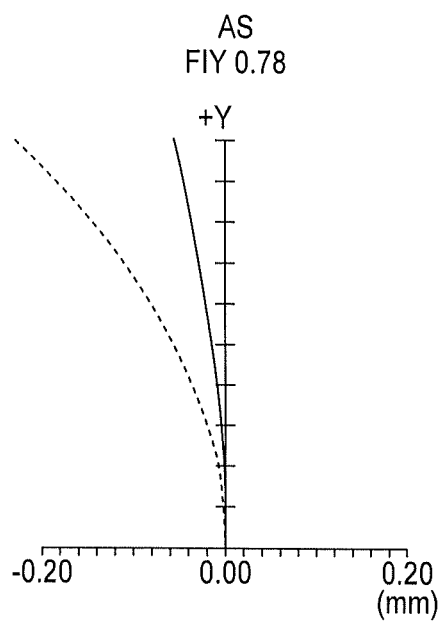
FIG. 20A, FIG. 20B, FIG. 20C, FIG. 20D, FIG. 20E, FIG. 20F, FIG. 20G, FIG. 20H, FIG. 20I, and FIG. 20J are aberration diagrams of the optical system for stereoscopic vision of the example 5.
Figure 20B:
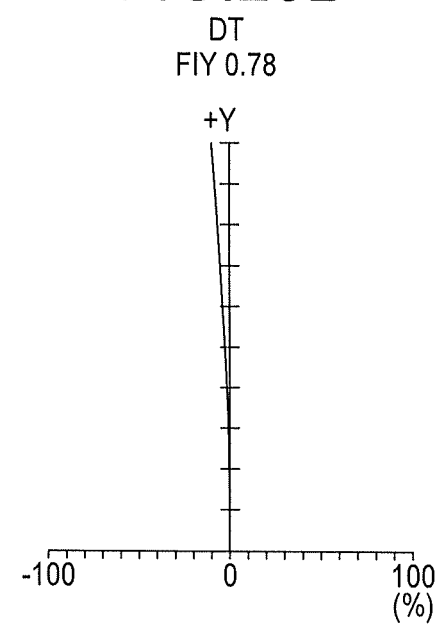
Figure 20C:
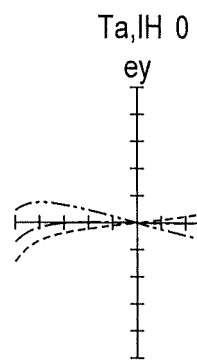
Figure 20D:
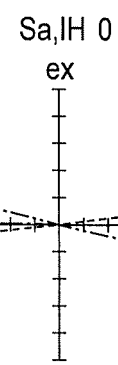
Figure 20E:
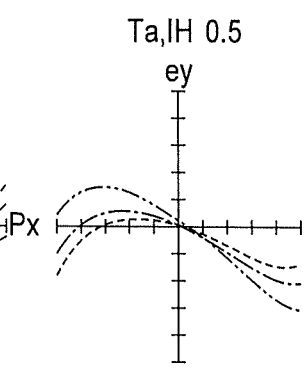
Figure 20F:
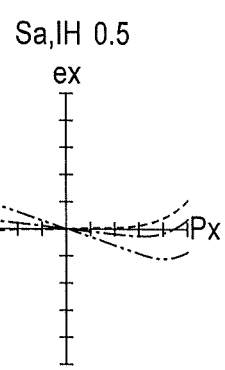
Figure 20G:
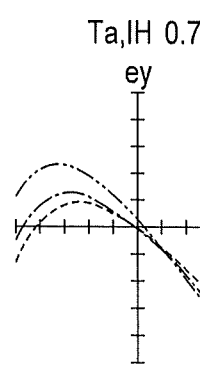
Figure 20H:
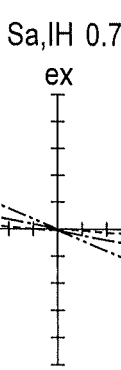
Figure 20I:
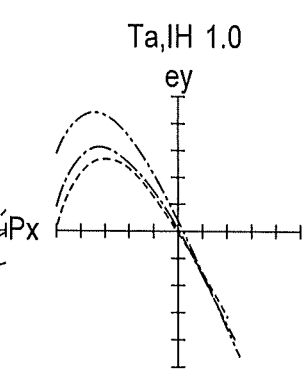
Figure 20J:
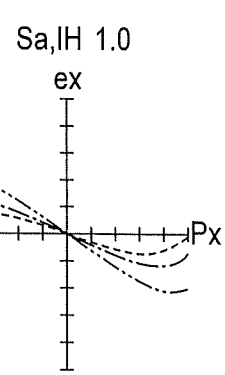
Figure 22A:
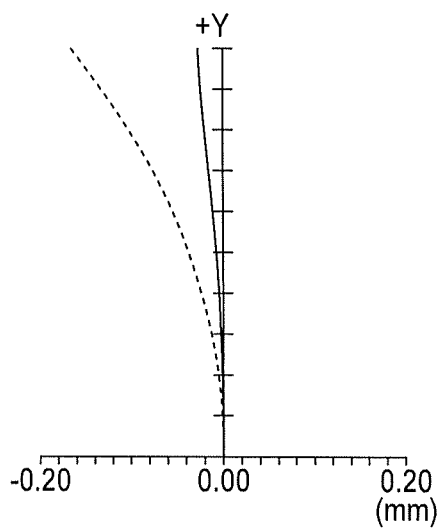
FIG. 22A, FIG. 22B, FIG. 22C, FIG. 22D, FIG. 22E, FIG. 22F, FIG. 22G, FIG. 22H, FIG. 22I, and FIG. 22J are aberration diagrams of the optical system for stereoscopic vision of the example 6.
Figure 22B:
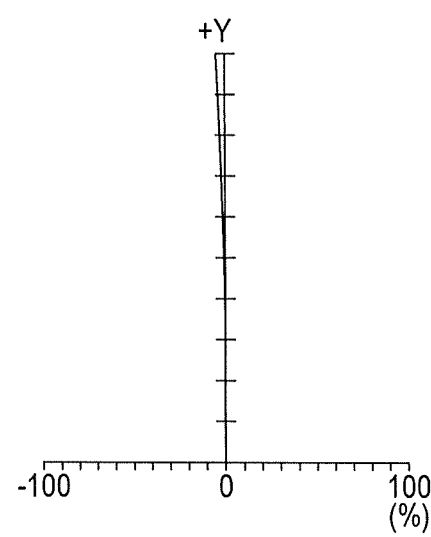
Figure 22C:
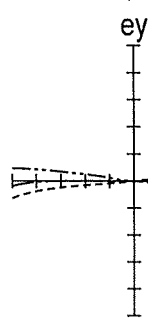
Figure 22D:
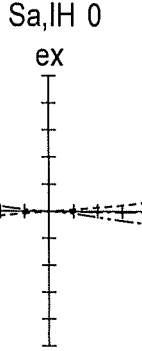
Figure 22E:
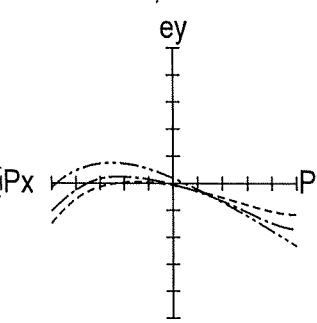
Figure 22F:
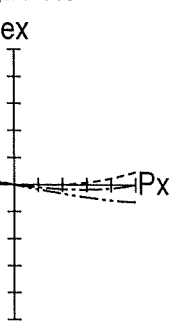
Figure 22G:
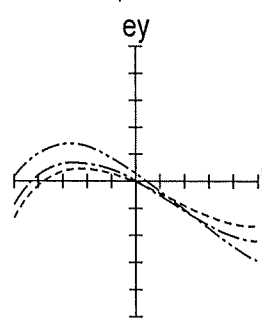
Figure 22H:
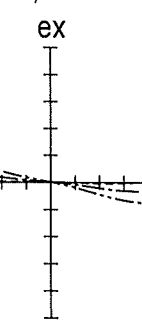
Figure 22I:
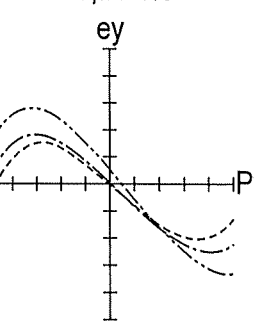
Figure 22J:
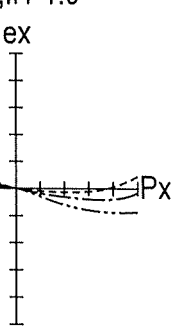

A specific arrangement of the common optical system is shown. FIG. 1A and FIG. 1B are lens cross-sectional views of the common optical system. FIG. 1A shows a lens cross-sectional view at the time of focusing to a far point. FIG. 1B shows a lens cross-sectional view at the time of focusing to a near point. The near point is a point positioned nearest to the optical system in a focusing range. The far point is a point positioned farthest from the optical system in the focusing range.

The common optical system includes a first optical system OBJ1 and a second optical system OBJ2. A central axis AXC is positioned between an optical axis AX1 of the first optical system OBJ1 and an optical axis AX2 of the second optical system OBJ2. The first optical system OBJ1 and the second optical system OBJ2 are disposed symmetrically with the central axis AXC interposed between the two. An optical element C1 is also shown in FIG. 1. However, the optical element C1 is not a component of the common optical system, but will be described together for convenience.

In the common optical system shown in FIG. 1A and FIG. 1B, the first optical system OBJ1 and the second optical system OBJ2 are the same optical system. Therefore, the first optical system OBJ1 will be described below.

The first optical system OBJ1 includes a planoconcave negative lens L1, a biconcave negative lens L2, a biconvex positive lens L3, a positive meniscus lens L4 having a convex surface directed toward an image side, a biconvex positive lens L5, a biconvex positive lens L6, a negative meniscus lens L7 having a convex surface directed toward an object side, a biconvex positive lens L8, a biconcave negative lens L9, and a biconvex positive lens L10.

The biconcave negative lens L2 and the biconvex positive lens L3 are cemented. The biconcave negative lens L9 and the biconvex positive lens L10 are cemented.

A stop S is disposed between the biconvex positive lens L5 and the biconvex positive lens L6. An optical element C1 is disposed on the object side of the planoconcave negative lens L1. A cover glass C2 is disposed on the image side of the biconvex positive lens L10.

The optical element C1 is one plane parallel plate. The optical element C1 is positioned to intersect both the optical axis AX1 of the first optical system OBJ1 and the optical axis AX2 of the second optical system OBJ2. The optical element C1 is not necessarily required.

In the common optical system, a position of the plano-concave negative lens L1 and a position of the negative meniscus lens L7 differ at the time of focusing to a far point and at the time of focusing to a near point. By making such arrangement, it is possible to make an inward angle at the time of focusing to the far point and an inward angle at the time of focusing to the near point, differ. In such manner, in the common optical system, focusing to objects positioned at different distances and changing the inward angle are carried out simultaneously by a movement of lenses.

In a method of changing a distance between the two stops S, the distance between the two stops S differs at the time of focusing to the near point and at the time of focusing to the far point. Moreover, as an object distance becomes shorter, it is necessary to narrow the distance between the two stops S. Therefore, in the method of changing the distance between the two stops S, the optical system becomes large in size.

Whereas, in the common optical system shown in FIG. 1A and FIG. 1B, the distance between the two stops is same at the time of focusing to the near point and at the time of focusing to the far point. Therefore, in the common optical system, even when the object distance becomes short, it is possible to suppress the optical system from becoming large in size.

In the common optical system shown in FIG. 1A and FIG. 1B, lenses are moved at two locations. The first location is between the optical element C1 and the biconcave negative lens L2, and one lens moves at this location. The second location is between the biconvex positive lens L6 and the biconvex positive lens L8, and one lens moves at this location.

However, the locations of moving the lenses are not restricted to the abovementioned two locations. Moreover, the number of lenses to be moved is not restricted to one. An arrangement may be made such that focusing to objects positioned at different distances and changing the inward angle occur simultaneously by moving a lens unit.

The focusing range is a range at an object space, and is a range in which it is possible to acquire a sharp image of an object when a lens in the optical system is moved along an optical axis.

The optical system for stereoscopic vision of the first embodiment includes the abovementioned common optical system. Further, each of the first optical system and the second optical system includes a stop and a plurality of lenses, and the plurality of lenses includes at least one movable lens unit which moves at the time of focusing. By the movement of the movable lens, at least focusing to a near point and a focusing to a far point is carried out, and at the time of focusing to the near point, both a first entrance pupil and a second entrance pupil are positioned on an image side of a position at the time of focusing to the far point.

Here, the first entrance pupil is an entrance pupil of the first optical system, the second entrance pupil is an entrance pupil of the second optical system, the near point is a point in the focusing range, positioned nearest to the optical system for stereoscopic vision, and the far point is a point in the focusing range, positioned farthest from the optical system for stereoscopic vision.

In the optical system for stereoscopic vision of the first embodiment, the first optical system includes at least one lens unit which moves at the time of focusing. Therefore, by the movement of the movable lens unit, it is possible to carry out at least focusing to the near point and focusing to the far point.

In the first optical system, a position of the first entrance pupil varies due to the movement of the lens unit which is moved at the time of focusing. In the second optical system, a position of the second entrance pupil varies due to the movement of the lens unit which is moved at the time of focusing. Due to the variation in position, the inward angle varies. Therefore, it is possible to make the inward angle at the time of focusing to the far point and the inward angle at the time of focusing to the near point, differ.

The movement of the first entrance pupil occurs due to a variation in a distance between a lens unit that moves at the time of focusing and the stop. The variation in the distance between the lens unit that moves at the time of focusing and the stop is a variation in a direction along the optical axis. Similar is true for the movement of the second entrance pupil. Therefore, compared to a method of changing the distance between the two stops, the size of the optical system does not become large in a direction orthogonal to the optical axis.

In the optical system for stereoscopic vision of the first embodiment, at the time of focusing to the near point, both the first entrance pupil and the second entrance pupil are positioned on the image side of positions at the time of focusing to the far point. Accordingly, it is possible to make an inward angle at the time of focusing to the near point an appropriate angle.

In such manner, according to the optical system for stereoscopic vision of the first embodiment, it is possible to make both the inward angle at the time of focusing to the far point and an inward angle at the time of focusing to the near point, appropriate angles while suppressing the optical system from becoming large in size.

Two images formed by the optical system for stereoscopic vision are captured by an imager of an image pickup apparatus. In the image pickup apparatus, the two captured images are displayed on a 3D (3-dimensional) monitor. Accordingly, it is possible to view an image of an object stereoscopically.

In a case in which the image pickup apparatus includes the optical system for stereoscopic vision of the first embodiment, it is possible to make small a difference which occurs between a stereoscopic effect at the time of focusing to the near point and a stereoscopic effect at the time of focusing to the far point, while suppressing the image pickup apparatus from becoming large in size. Therefore, according to the image pickup apparatus which includes the optical system for stereoscopic vision of the first embodiment, even when the stereoscopic vision is carried out with an image at the time of focusing to the far point and even the stereoscopic vision is carried out with an image at the time of focusing to the near point, it is possible to observe a stereoscopic image having an appropriate depth.

The optical system for stereoscopic vision of the second embodiment includes the abovementioned common optical system and an optical element. Further, a first optical system and a second optical system are disposed on an image side of the optical element, and the optical element is positioned to intersect both an optical axis of the first optical system and an optical axis of the second optical system. Each of the first optical system and the second optical system includes a stop and at least two movable lens units which move at the time of focusing. The two movable lens units includes in order from the object side, a first movable lens unit and a second movable lens unit, at least focusing to a near point and focusing to a far point is carried out by the movement of at least the second movable lens unit, at the time of focusing from a far point to a near point, the first movable lens unit moves from the object side toward the image side, and the following conditional expression (1) is satisfied:

$$-0.1 < FL1m/FLc < 0.1 \quad (1)$$

where,

FLc denotes a focal length of the optical element,

FL1m denotes a focal length of the first movable lens unit in the first optical system and a focal length of the first movable lens unit in the second optical system, the near point is a point in a focusing range, positioned nearest to the optical system for stereoscopic vision, and the far point is a point in the focusing range, positioned farthest from the optical system for stereoscopic vision.

In the optical system for stereoscopic vision of the second embodiment, the first optical system includes at least the first movable lens unit and the second movable lens unit. In this case, it is possible to carry out at least focusing to the near point and focusing to the far point by at least second movable lens unit. Similar is true for the second optical system.

In the first optical system, the position of the first entrance pupil varies due to the movement of at least the first movable lens unit. In the second optical system, the position of the second entrance pupil varies due to the movement of at least the first movable lens unit. Due to the variation, the inward angle varies. Therefore, it is possible to make the inward angle at the time of focusing to the far point and the inward angle at the time of focusing to the near point, differ.

In the optical system for stereoscopic vision of the second embodiment, due to the movement of the first movable lens unit and the second movable lens unit, focusing to objects positioned at different distances and change of the inward angle occur simultaneously.

Focusing to objects positioned at different distances is carried out by the movement of at least the second movable lens unit. However, since the first movable lens unit is moving at the time of focusing, it is not to say that the movement of the first movable lens unit does not contribute at all to focusing to objects positioned at different distances.

Moreover, changing the inward angle is carried out by the movement of at least the first movable lens unit. However, since the second movable lens unit moves at the time of focusing, it is not to say that the movement of the second movable lens unit does not contribute at all to changing the inward angle.

The movement of the first entrance pupil occurs at least due to a variation in a distance between the first movable lens unit and the stop. The variation in the distance between the first movable lens unit and the stop is a variation in a direction along the optical axis. Similar is true for the movement of the second entrance pupil. Therefore, as compared to a method of changing the distance between the two stops, the optical system does not become large in a direction orthogonal to the optical axis.

Moreover, in a case of capturing two images formed by the optical system for stereoscopic vision by imagers, it is possible to make small a distance between centers of the two imagers. As it is possible to take a large image pickup area in a fixed outer diameter, it is possible to secure a wide field of view.

In the first optical system, the first movable lens unit is positioned on the object side of the second movable lens unit. The first movable lens unit, at the time of focusing from the far point to the near point, moves from the object side toward the image side. Accordingly, in the first optical system, it is possible to secure appropriately a distance from the far point up to the first entrance pupil and a distance from the near point to the first entrance pupil. Similar is true for the second optical system.

In a case of exceeding an upper limit value of conditional expression (1) or falling below a lower limit value of conditional expression (1), the refractive power of the optical element becomes excessively large with respect to the refractive power of the first movable lens unit in the first optical system. Consequently, it is not possible to achieve adequately an effect of moving the first entrance pupil. Or, the refractive power of the optical element becomes excessively large with respect to the refractive power of the first movable lens unit in the second optical system. Consequently, it is not possible to achieve adequately an effect of moving the second entrance pupil.

Moreover, aberration correction also becomes difficult. Particularly, an off-axis aberration such as, a coma and a distortion, is susceptible to occur largely. Therefore, exceeding the upper limit value of conditional expression (1) or falling below the lower limit value of conditional expression (1) is not preferable.

As mentioned above, in the image pickup apparatus, it is possible to view the image of the object stereoscopically. In a case in which the image pickup apparatus includes the optical system for stereoscopic vision of the second embodiment, by satisfying conditional expression (1), even when the stereoscopic vision is carried out with the image at the time of focusing to the near point, it is possible to observe a stereoscopic image having an appropriate depth.

The optical system for stereoscopic vision of a third embodiment includes the abovementioned common optical system. Further, each of the first optical system and the second optical system includes a stop and a movable lens unit which moves at the time of focusing, at least focusing to a near point and focusing to a far point are carried out by a movement of the movable lens unit, and a focus position is changed by moving the movable lens unit while making satisfy the following conditional expression (2):

$$0.1 < a \tan(De/Loben) - a \tan(De/Lobef) < 0.8 \quad (2)$$

where,

De denotes a distance between a center of a first entrance pupil and the center of a second entrance pupil, Loben denotes a distance on an optical axis from a position of the near point up to a position of the first entrance pupil at the time of focusing to the near point and a distance on the optical axis from the position of the near point up to a position of the second entrance pupil at the time of focusing to the near point, and Lobef denotes a distance on the optical axis from a position of the far point up to a position of the first entrance pupil at the time of focusing to the far point and a distance on the optical axis from the position of the far point up to a position of the second entrance pupil at the time of focusing to the far point, and here the first entrance pupil is an entrance pupil of the first optical system, the second entrance pupil is an entrance pupil of the second optical system, the near point is a point in a focusing range, positioned nearest to the optical system for stereoscopic vision, and the far point is a point in the focusing range, positioned farthest from the optical system for stereoscopic vision.

In the optical system for stereoscopic vision of the third embodiment, the first optical system includes the movable lens unit. Consequently, it is possible to carry out at least focusing to the near point and focusing to the far point by the movement of the movable lens unit. Similar is true for the second optical system.

In the first optical system, the position of the first entrance pupil varies due to the movement of the movable lens unit. In the second optical system, the position of the second entrance pupil varies due to the movement of the movable lens unit. Due to the variation in the position, the inward angle varies. Therefore, it is possible to make the inward angle at the time of focusing to the far point and an inward angle at the time of focusing to the near point, differ.

The movement of the first entrance pupil occurs due to variation in a distance between the movable lens unit and the stop. The variation in the distance between the movable lens unit and the stop is a variation in a direction along the optical axis. Similar is true for the movement of the second entrance pupil. Therefore, as compared to the distance of the two stops, the optical system does not become large in size in a direction orthogonal to the optical axis. Moreover, it is possible to secure a wide field of view.

As mentioned above, in the image pickup apparatus, it is possible to view the image of the object stereoscopically. It is desirable that when an image at the time of focusing to the far point is displayed on a 3D monitor with general conditions, an adequate resolution in a direction of depth be secured in the stereoscopic image. For this, it is necessary to make a distance between a center of the first entrance pupil and a center of the second entrance pupil not less than a certain distance.

By satisfying conditional expression (2), it is possible to secure appropriately the distance between the center of the first entrance pupil and the center of the second entrance pupil. Consequently, in the stereoscopic vision of the image at the time of focusing to the far point, it is possible to not let the stereoscopic image be extended excessively in the direction of depth in the stereoscopic vision of the image at the time of focusing to the near point, while securing a high resolution in the direction of depth in the stereoscopic vision of the image at the time of focusing to the far point. As a result, it is possible to realize an optical system for stereoscopic vision which does not cause fatigue to an observer.

In a case of exceeding an upper limit value of conditional expression (2), a difference between the inward angle at the time of focusing to the far point and the inward angle at the time of focusing to the near point becomes excessively large. In this case, in the stereoscopic vision of the image at the time of focusing to the near point, the stereoscopic image is extended excessively in the direction of depth. As a result, it is susceptible to cause fatigue to the observer. Therefore, exceeding the upper limit value of conditional expression (2) is not preferable.

In a case of falling below a lower limit value of conditional expression (2), the difference between the inward angle at the time of focusing to the far point and the inward angle at the time of focusing to the near point becomes excessively small. In this case, for achieving an adequate stereoscopic effect in the stereoscopic vision of the image at the time of focusing to the near point, it is necessary to move both the position of the first entrance pupil and the position of the second entrance pupil substantially toward the image side at the time of focusing to the near point.

However, when the position of the first entrance pupil and the position of the second entrance pupil are moved substantially toward the image side, it becomes difficult to achieve both of securing a wide angle of view and small-sizing of the optical system. Moreover, correction of an off-axis aberration also becomes difficult. Therefore, falling below the lower limit value of conditional expression (2) is not preferable.

The optical system for stereoscopic vision of the fourth embodiment includes the abovementioned common optical system and the optical element. Further, the first optical system and the second optical system are disposed on the image side of the optical element, and each of the first optical system and the second optical system includes a stop and a lens unit having a negative refractive power. At the time of focusing from the far point to the near point, the optical element is fixed, and the lens unit having a negative refractive power moves from the object side toward the image side, and the following conditional expression (3) is satisfied:

$$5.0<(Lnobf-Lnobn)/Dax<50.0 \quad (3)$$

where,

Dax denotes a distance between an optical axis of the first optical system and an optical axis of the second optical system, Lnobf denotes a distance on the optical axis from a surface nearest to an object of the lens unit having a negative refractive power in the first optical system at the time of focusing to the far point up to a position of the far point, and a distance on the optical axis from a surface nearest to the object of the lens unit having a negative refractive power in the second optical system at the time of focusing to the far point up to the position of the far point, and Lnobn denotes a distance on the optical axis from the surface nearest to the object of the lens unit having a negative refractive power in the first optical at the time of focusing to the near point system up to a position of the near point, and a distance on the optical axis from the surface nearest to the object of the lens unit having a negative refractive power in the second optical system at the time of focusing to the near point up to the position of the near point, and here the near point is a point in a focusing range, positioned nearest to the optical system for stereoscopic vision, and the far point is a point in the focusing range, positioned farthest from the optical system for stereoscopic vision.

In the optical system for stereoscopic vision of the fourth embodiment, the first optical system includes a lens unit having a negative refractive power as the movable lens unit. Consequently, due to the movement of the lens unit having a negative refractive power, it is possible to carry out at least focusing to the near point and focusing to the far point. Similar is true for the second optical system.

In the first optical system, a position of the first entrance pupil varies due to the movement of the lens unit having a negative refractive power. In the second optical system, a position of the second entrance pupil varies due to the movement of the lens unit having a negative refractive power. Due to the variation in the position, the inward angle varies. Therefore, it is possible to make the inward angle at the time of focusing to the far point and the inward angle at the time of focusing to the near point, differ.

The movement of the first entrance pupil occurs due to a variation in a distance between the lens unit having a negative refractive power and the stop. The variation in the distance between the lens unit having a negative refractive power and the stop is a variation in a direction along the optical axis. Similar is true for the movement of the second entrance pupil. Therefore, compared to a method of changing the distance between the two stops, the size of the optical system does not become large in a direction orthogonal to the optical axis. Moreover, it is possible to secure a wide field of view.

At the time of focusing from the far point to the near point, the optical element is fixed, and both the lens unit having a negative refractive power in the first optical system and the lens unit having a negative refractive power in the second optical system move from the object side toward the image side.

As mentioned above, in the image pickup apparatus, it is possible to view the image of the object stereoscopically. It is desirable that when an image at the time of focusing to the far point is displayed on a 3D monitor with general conditions, an adequate resolution in a direction of depth be secured in the stereoscopic image. For this, it is necessary to make a distance between a center of the first entrance pupil and a center of a second entrance pupil not less than a certain distance.

At the time of focusing from the far point to the near point, both the lens unit having a negative refractive power in the first optical system and the lens unit having a negative refractive power in the second optical system move from the object side toward the image side. By moving the lens units in such manner and by satisfying conditional expression (3), it is possible to secure adequately the distance between the center of the first entrance pupil and the center of the second entrance pupil. Consequently, in the stereoscopic vision of the image at the time of focusing to the near point, it is possible to not let the stereoscopic image be extended excessively in the direction of depth in the stereoscopic vision of an image at the time of focusing to the near point. As a result, it is possible to realize an optical system for stereoscopic vision which does not cause fatigue to the observer.

In a case of exceeding an upper limit value of conditional expression (3), the difference between the inward angle at the time of focusing to the far point and the inward angle at the time of focusing to the near point becomes excessively large. In this case, in the stereoscopic vision of the image at the time of focusing to the near point, the stereoscopic image is extended excessively in the direction of depth. As a result, it is susceptible to cause fatigue to the observer. Therefore, exceeding the upper limit value of conditional expression (3) is not preferable.

In a case of falling below a lower limit value of conditional expression (3), the difference between the inward angle at the time of focusing to the far point and the inward angle at the time of focusing to the near point becomes excessively small. In this case, both a moving distance of the lens unit having a negative refractive power in the first optical system and a moving distance of the lens unit having a negative refractive power in the second optical system becomes large. Consequently, it becomes difficult to achieve both of small-sizing of the optical system and securing a favorable imaging performance. Regarding the imaging performance, particularly, a favorable correction of an off-axis aberration such as the coma becomes difficult.

Moreover, by imparting negative refractive power to the movable lens unit, it is possible to make the optical system an optical system with a wide angle of view.

In the optical system for stereoscopic vision of the second embodiment, it is preferable that the following conditional expression (4) be satisfied:

$$0.05 < (Lc1mn - Lc1mf)/TTL < 0.25 \quad (4)$$

where, $Lc1mn$ denotes a distance on an optical axis from an object-side surface of the optical element up to a lens surface positioned nearest to an object of the first movable lens unit in the first optical system at the time of focusing to the near point, and a distance on the optical axis from the object-side surface of the optical element up to a lens surface positioned nearest to the object of the first movable lens unit in the second optical system at the time of focusing to the near point, $Lc1mf$ denotes a distance on the optical axis from the object-side surface of the optical element up to the lens surface positioned nearest to the object of the first movable lens unit in the first optical system at the time of focusing to the far point, and a distance on the optical axis from the object-side surface of the optical element up to the lens surface positioned nearest to the object of the first movable lens unit in the second optical system at the time of focusing to the far point, and TTL denotes a distance on the optical axis from the object-side surface of the optical element up to an image plane.

As mentioned above, in the optical system for stereoscopic vision of the second embodiment, at the time of focusing from the far point to the near point, the first movable lens unit in the first optical system moves from the object side toward the image side. Accordingly, it is possible to maintain a distance from the far point up to the first entrance pupil and a distance from the near point up to the first entrance pupil. Similar is true for the second optical system.

Consequently, it is possible to maintain a diameter of the first optical system and a diameter of the second optical system small while making possible an observation of a stereoscopic image having an appropriate depth in the stereoscopic vision of the image at the time of focusing to the near point.

In a case of exceeding an upper limit value of conditional expression (4), an amount of movement of the first movable lens unit in the first optical system with respect to the optical element becomes excessively large. In this case, in the first optical system, a fluctuation in aberration due to the movement of the first movable lens unit, and particularly, an amount of fluctuation in an off-axis aberration such as a curvature of field in particular, becomes large. Similar is true for the second optical system. Therefore, exceeding the upper limit value of conditional expression (4) is not preferable.

In a case of falling below a lower limit value of conditional expression (4), the amount of movement of the first movable lens unit in the first optical system with respect to the optical element becomes excessively small. In this case, in the first optical system, it is not possible to carry out an adequate adjustment of the stereoscopic effect by the movement of the first movable lens unit. Similar is true for the second optical system. Therefore, falling below the lower limit value of conditional expression (4) is not preferable.

It is preferable that the optical system for stereoscopic vision of the first embodiment and the optical system for stereoscopic vision of the second embodiment include the optical element on the object side of the first optical system and the second optical system, and the following conditional expression (5) be satisfied:

$$0.5 < Lcef/IH < 10.0 \quad (5)$$

where, $Lcef$ denotes a distance on the optical axis from the object-side surface of the optical element up to the position of the first entrance pupil at the time of focusing to the far point, and a distance on the optical axis from the object-side surface of the optical element up to the position of the second entrance pupil at the time of focusing to the far point, and IH denotes the maximum image height.

In a case of exceeding an upper limit value of conditional expression (5), both the position of the first entrance pupil and the position of the second entrance pupil are drawn excessively close to the image side. In this case, since a diameter of an object-side surface of the optical element becomes large, small-sizing of the optical system becomes difficult. Therefore, it exceeding the upper limit value of conditional expression (5) is not preferable.

In a case of falling below a lower limit value of conditional expression (5), both the position of the first entrance pupil and the position of the second entrance pupil are drawn excessively close to the object side. Consequently, in a case in which the angle of view is made wide, it becomes difficult to suppress the distortion. When the distortion becomes excessively large, it becomes difficult to achieve a favorable resolution performance in a periphery of the stereoscopic image at the time of viewing the image of the object stereoscopically. Moreover, at the time of viewing the image of the object stereoscopically, it is not possible to achieve an appropriate stereoscopic effect in the periphery of the stereoscopic image. Therefore, falling below the lower limit value of conditional expression (5) is not preferable.

In the optical system for stereoscopic vision of the second embodiment and the optical system for stereoscopic vision of the fourth embodiment, it is preferable that the following conditional expression (5) be satisfied:

$$0.5 < Lcef/IH < 10.0 \quad (5)$$

where,

Lcef denotes the distance on the optical axis from the object-side surface of the optical element up to the position of the first entrance pupil at the time of focusing to the far point, and the distance on the optical axis from the object-side surface of the optical element up to the position of the second entrance pupil at the time of focusing to the far point, and IH denotes the maximum image height, and here the first entrance pupil is an entrance pupil of the first optical system, and the second entrance pupil is an entrance pupil of the second optical system.

A technical significance of conditional expression (5) is as mentioned above. In the optical system for stereoscopic vision of the second embodiment and the optical system for stereoscopic vision of the fourth embodiment, it is preferable that both the first optical system and the second optical system satisfy conditional expression (5).

It is preferable that the optical system for stereoscopic vision of the first embodiment and the optical system for stereoscopic vision of the third embodiment include the optical element on the object side of the first optical system and the second optical system, and the following conditional expression (6) be satisfied:

$$0.3 < Lcef/De < 2.0 \quad (6)$$

where,

Lcef denotes the distance on the optical axis from the object-side surface of the optical element up to the position of the first entrance pupil at the time of focusing to the far point, and the distance on the optical axis from the object-side surface of the optical element up to the position of the second entrance pupil at the time of focusing to the far point, and De denotes the distance between the center of the first entrance pupil and the center of the second entrance pupil.

In a case of exceeding an upper limit value of conditional expression (6), both the position of the first entrance pupil and the position of the second entrance pupil are drawn excessively close to the image side. In this case, a distance from the far point up to the first entrance pupil and a distance from the near point up to the second entrance pupil become short with respect to the distance between the center of the first entrance pupil and the center of the second entrance pupil. Consequently, in the stereoscopic vision of the image at the time of focusing to the far point, it becomes difficult to secure a high resolution in the direction of depth.

In a case of falling below a lower limit value of conditional expression (6), both the position of the first entrance pupil and the position of the second entrance pupil are drawn excessively close to the object side. Consequently, in a case in which the angle of view is made wide, it becomes difficult to suppress the distortion.

When the distortion becomes excessively large, it becomes difficult to achieve a favorable resolution performance in a periphery of the stereoscopic image at the time of viewing the image of the object stereoscopically. Moreover, at the time of viewing the image of the object stereoscopically, it is not possible to achieve an appropriate stereoscopic image in a periphery of the stereoscopic image. Therefore, it falling below the lower limit value of conditional expression (6) is not preferable.

In the optical system for stereoscopic vision of the second embodiment and the optical system for stereoscopic vision of the fourth embodiment, it is preferable that the following conditional expression (6) be satisfied:

$$0.3 < Lcef/De < 2.0 \quad (6)$$

where,

Lcef denotes the distance on the optical axis from the object-side surface of the optical element up to the position of the first entrance pupil at the time of focusing to the far point, and the distance on the optical axis from the object-side surface of the optical element up to the position of the second entrance pupil at the time of focusing to the far point, and De denotes the distance between the center of the first entrance pupil and the center of the second entrance pupil, and here the first entrance pupil is an entrance pupil of the first optical system, and the second entrance pupil is an entrance pupil of the second optical system.

A technical significance of conditional expression (6) is as mentioned above. In the optical system for stereoscopic vision of the second embodiment and the optical system for stereoscopic vision of the fourth embodiment, it is preferable that both the first optical system and the second optical system satisfy conditional expression (6).

It is preferable that the optical system for stereoscopic vision of the first embodiment and the optical system for stereoscopic vision of the third embodiment include the optical element on the object side of the first optical system and the second optical system, and the following conditional expression (7) be satisfied:

$$0.04 < Lcef/TTL < 0.2 \quad (7)$$

where,

Lcef denotes the distance on the optical axis from the object-side surface of the optical element up to the position of the first entrance pupil at the time of focusing to the far point, and the distance on the optical axis from the object-side surface of the optical element up to the position of the second entrance pupil at the time of focusing to the far point, and TTL denotes the distance on the optical axis from the object-side surface of the optical element up to the image plane.

A technical significance of conditional expression (7) is same as the technical significance of conditional expression (5). In the optical system for stereoscopic vision of the first embodiment and the optical system for stereoscopic vision of the third embodiment, it is preferable that both the first optical system and the second optical system satisfy conditional expression (7).

In the optical system for stereoscopic vision of the second embodiment and the optical system for stereoscopic vision of the fourth embodiment, it is preferable that the following conditional expression (7) be satisfied:

$$0.04 < Lcef/TTL < 0.2 \quad (7)$$

where,

Lcef denotes the distance on the optical axis from the object-side surface of the optical element up to the position of the first entrance pupil at the time of focusing to the far point, and the distance on the optical axis from the object-side surface of the optical element up to the position of the second entrance pupil at the time of focusing to the far point, and TTL denotes the distance on the optical axis from the object-side surface of the optical element up to the image plane, and here the first entrance pupil is an entrance pupil of the first optical system, and the second entrance pupil is an entrance pupil of the second optical system.

A technical significance of conditional expression (7) is as mentioned above.

In the optical systems for stereoscopic vision from the optical system for stereoscopic vision of the first embodiment up to the optical system for stereoscopic vision of the fourth embodiment (hereinafter, referred to as 'optical system for stereoscopic vision of the present embodiment'), it is preferable that the following conditional expression (8) be satisfied:

$$1.0 < FLn/FLf < 2.0 \quad (8)$$

where,

FLf denotes a focal length of the first optical system and a focal length of the second optical system, at the time of focusing to the far point, and FLn denotes a focal length of the first optical system and a focal length of the second optical system, at the time of focusing to the near point.

In a case of exceeding an upper limit value of conditional expression (8), a focal length of the overall optical system for stereoscopic vision at the time of focusing to the near point becomes excessively long. In this case, at the time of focusing to the near point, it becomes difficult to achieve both of small-sizing of the optical system and widening of the field of view. Moreover, at the time of focusing from the far point to the near point, the distortion is susceptible to fluctuate largely. When the distortion fluctuates largely, the stereoscopic effect in a peripheral portion of the stereoscopic image varies largely at the time of viewing the image of the object stereoscopically. Therefore, exceeding the upper limit value of conditional expression (8) is not preferable.

In a case of falling below a lower limit value of conditional expression (8), the focal length of the overall optical system for stereoscopic vision at the time of focusing to the near point becomes excessively short. In this case, the diameter of the object-side surface of the optical element becomes excessively large. Therefore, falling below the lower limit value of conditional expression (8) is not preferable.

In the optical system for stereoscopic vision of the present embodiment, it is preferable that each of the first optical system and the second optical system include in order from the object side, a first lens unit having a negative refractive power, a second lens unit having a positive refractive power, a third lens unit, and a fourth lens unit.

By making such arrangement, it is possible to suppress both an occurrence of an axial aberration and an occurrence of an off-axis aberration even when the angle of view is made wide. Moreover, in the first optical system, particularly by the optical element and the first lens unit, it is possible to prevent a height of a light ray from becoming high. Similar is true for the second optical system.

In the optical system for stereoscopic vision of the second embodiment, it is preferable that the optical element have a symmetrical shape with respect to a central axis which is positioned between the optical axis of the first optical system and the optical axis of the second optical system. Moreover, it is preferable that the optical system for stereoscopic vision of the present embodiment include the optical element on the object side of the first optical system and the second optical system, and the optical element has a symmetrical shape with respect to the central axis which is positioned between the optical axis of the first optical system and the optical axis of the second optical system.

By making such arrangement, it is possible to balance a decentration aberration which occurs in the first optical system and a decentration aberration which occurs in the second optical system. The central axis can be deemed as an optical axis of the optical system for stereoscopic vision.

It is preferable that the optical system for stereoscopic vision of the present embodiment include the optical element on the object side of the first optical system and the second optical system, and the optical element be fixed at the time of focusing.

By making such arrangement, in the first optical system, it is possible to maintain appropriately both the distance from the near point up to the first entrance pupil and the distance from the far point up to the first entrance pupil. Similar is true for the second optical system.

It is preferable that the optical system for stereoscopic vision of the present embodiment include the optical element on the object side of the first optical system and the second optical system, and the optical element be a plane parallel plate.

In the optical element, an effective light ray incident on the first optical system and an effective light ray incident on the second optical system overlap. An overlapping region is mainly a region near the central axis. A position of this region is decentered with respect to the optical axis of the first optical system and the optical axis of the second optical system. Consequently, the decentration aberration is susceptible to occur. By making the optical element a plane parallel plate, it is possible to suppress an occurrence of the decentration aberration. Particularly, at the time of focusing to the near point, it is possible to suppress the occurrence of the decentration aberration.

In the optical system for stereoscopic vision of the second embodiment, it is preferable that the first movable lens unit be a negative lens.

It is preferable that both the first movable lens unit of the first optical system and the first movable lens unit of the second optical system be negative lenses. By making such arrangement, at the time of focusing from the far point to the near point, it is possible to move both the position of the first entrance pupil and the position of the second entrance pupil with respect to the optical element, toward the image side. By moving the two entrance pupils, it is possible to adjust the inward angle and to narrow the angle of view of the optical system. Since it is possible to narrow the angle of view of the optical system, it is possible to make small a diameter of the optical system.

In the optical system for stereoscopic vision of the present embodiment, it is preferable that the third lens unit move at the time of focusing.

It is preferable that both the third lens unit in the first optical system and the third lens unit in the second optical system move at the time of focusing. It is possible to move both the first lens unit of the first optical system and the first lens unit of the second optical system at the time of focusing. In this case, by moving the third lens unit with the movement of the first lens unit, it is possible to carry out focusing from the far point to the near point while suppressing the fluctuation in the curvature of field.

In the optical system for stereoscopic vision of the present embodiment, it is preferable that the third lens unit have a negative refractive power and move from the object side toward the image side at the time of focusing from the far point to the near point.

It is preferable that the both the third lens unit in the first optical system and the third lens unit in the second optical system have a negative refractive power and move from the object side toward the image side at the time of focusing from the far point to the near point. By making such arrangement, it is possible to secure adequately a distance from a lens surface positioned nearest to an image in the fourth lens unit up to an image plane.

In the optical system for stereoscopic vision of the present embodiment, it is preferable that the third lens unit have a positive refractive power and move from the image side toward the object side at the time of focusing from the far point to the near point.

It is preferable that both the third lens unit in the first optical system and the third lens unit in the second optical system have a refractive power and move from the image side toward the object side at the time of focusing from the far point to the near point. By making such arrangement, it is possible to shorten the overall length of the optical system.

It is preferable that the optical system for stereoscopic vision include the optical element on the object side of the first optical system and the second optical system, and the following conditional expression (9) be satisfied:

$$-0.1 < IH/FLc < 0.1 \quad (9)$$

where,

FLc denotes a focal length of the optical element, and IH denotes the maximum image height.

By satisfying conditional expression (9), it is possible to suppress an occurrence of the decentration aberration. As a result, it is possible to achieve a favorable imaging performance.

In the optical system for stereoscopic vision of the present embodiment, it is preferable that the following conditional expression (10) be satisfied:

$$-3.0 < FL1G/IH < -1.0 \quad (10)$$

where,

FL1G denotes a focal length of the first lens unit in the first optical system and a focal length of the first lens unit in the second optical system, and IH denotes the maximum image height.

In a case of exceeding an upper limit value of conditional expression (10), the refractive power of the first lens unit in the first optical system becomes excessively large. In this case, aberrations such as the coma and the distortion occur largely. Similar is true for the second optical system. Therefore, exceeding the upper limit value of conditional expression (10) is not preferable.

In a case of falling below a lower limit value of conditional expression (10), when the angle of view is made wide, the lens becomes large in size. Therefore, falling below the lower limit value of conditional expression (10) is not preferable.

In the optical system for stereoscopic vision of the present embodiment, it is preferable that the following conditional expression (11) be satisfied:

$$1.5 < FL2G/IH < 7.0 \quad (11)$$

where,

FL2G denotes a focal length of the second lens unit in the first optical system and a focal length of the second lens unit in the second optical system, and IH denotes the maximum image height.

In a case of exceeding an upper limit value of conditional expression (11), an angle of a light ray emerged from the second lens unit in the first optical system with respect to the optical axis becomes excessively large. Consequently, when light emerged from the second lens unit is incident on the third lens unit, an off-axis aberration, particularly, the coma, is susceptible to occur. Similar is true for the second optical system. Therefore, it exceeding the upper limit value of conditional expression (11) is not preferable.

In a case of falling below a lower limit value of conditional expression (11), it is not possible to converge adequately an axial light ray emerged from the second lens unit in the first optical system. Consequently, a lens diameter in the third lens unit becomes large. Similar is true for the second optical system. Therefore, falling below the lower limit value of conditional expression (11) is not preferable.

In the optical system for stereoscopic vision of the present embodiment, it is preferable that the following conditional expression (12) be satisfied:

$$-10.0 < FL3G/IH < 20.0 \quad (12)$$

where,

FL3G denotes a focal length of the third lens unit in the first optical system and a focal length of the third lens unit in the second optical system, and IH denotes the maximum image height.

By satisfying conditional expression (12), it is possible to suppress both a fluctuation in aberration due to the movement at the time of focusing to the far point and a fluctuation in aberration due to the movement of the lens unit at the time of focusing to the near point to small. Conditional expression (12) is a conditional expression preferable for suppressing the fluctuation in the curvature of field.

In the optical system for stereoscopic vision of the present embodiment, it is preferable that the following conditional expression (13) be satisfied:

$$2.0 < FL4G/IH < 40.0 \quad (13)$$

where,

FL4G denotes a focal length of the fourth lens unit in the first optical system and a focal length of the fourth lens unit in the second optical system, and IH denotes the maximum image height.

By satisfying conditional expression (13), it is possible to carry out both small-sizing of the optical system and favorable correction of the off-axis aberration.

In the optical system for stereoscopic vision of the present embodiment, it is preferable that the stop be disposed in the second lens unit.

By making such arrangement, in the first optical system and the second optical system, the respective stops are disposed at a substantial center of the optical system. In this case, a height of a light ray on both sides of the stop does not differ extremely. As a result, it is possible to suppress the height of a light ray between the optical element and the fourth lens unit in a balanced manner. Thus, the stop being disposed in the second lens unit is favorable for small-sizing the optical system.

In the optical system for stereoscopic vision of the present embodiment, it is preferable that the stop move together with the third lens unit.

By making such arrangement, in the first optical system and the second optical system, the respective stops are disposed at a substantial center of the optical system. In this case, the height of a light ray on both sides of the stop does not differ extremely. As a result, it is possible to suppress the height of a light ray between the optical element and the fourth lens unit in a balanced manner. Thus, the stop moving together with the third lens unit is preferable for small-sizing.

In the optical system for stereoscopic vision of the present embodiment, it is preferable that the first optical system and the second optical system be the same optical system.

By making such arrangement, it is possible to suppress a difference between an imaging magnification of the first optical system and an imaging magnification of the second optical system. As a result, it is possible to suppress a vertical shift in the stereoscopic image at the time of viewing the image of the object is viewed stereoscopically. Therefore, it is possible to reduce fatigue of the observer. The vertical shift is a shift in a direction orthogonal to the parallax direction.

In the optical system for stereoscopic vision of the present embodiment, it is preferable that the following conditional expression (14) be satisfied:

$$0.1 < (MG1Gf/MG1Gn)/(MG3Gf/MG3Gn) < 0.5 \quad (14)$$

where,

MG1Gn denotes a lateral magnification of the first lens unit in the first optical system and a lateral magnification of the first lens unit in the second optical system at the time of focusing to the near point, MG1Gf denotes a lateral magnification of the first lens unit in the first optical system and a lateral magnification of the first lens unit in the second optical system at the time of focusing to the far point, MG3Gn denotes a lateral magnification of the third lens unit in the first optical system and a lateral magnification of the third lens unit in the second optical system at the time of focusing to the near point, and MG3Gf denotes a lateral magnification of the third lens unit in the first optical system and a lateral magnification of the third lens unit in the second optical system at the time of focusing to the far point.

In a case of exceeding an upper limit value of conditional expression (14), a fluctuation in the height of a light ray in the first lens unit becomes excessively large when a focus position is changed. Moreover, correction of an off-axis aberration, particularly, correction of the coma and correction of the curvature of field become difficult. Therefore, exceeding the upper limit value of conditional expression (14) is not preferable.

In a case of falling below a lower limit value of conditional expression (14), in the first optical system, it is not possible to achieve an adequate effect of increase in magnification by the movement of the first lens unit and an effect of adjustment of the stereoscopic effect by the movement of the first entrance pupil. Similar is true for the second optical system. Therefore, falling below the lower limit value of conditional expression (14) is not preferable. The effect of increase in magnification is an effect of making the lateral magnification large.

In the optical system for stereoscopic vision of the present embodiment, it is preferable that the following conditional expression (15) be satisfied:

$$2.5 < MGn/MGf < 11.0 \quad (15)$$

where,

MGn denotes a lateral magnification of the first optical system and a lateral magnification of the second optical system at the time of focusing to the near point, and MGf denotes a lateral magnification of the first optical system and a lateral magnification of the second optical system at the time of focusing to the far point.

In a case of exceeding an upper limit value of conditional expression (15), it becomes difficult to correct the off-axis aberration adequately. Moreover, the observation field becomes excessively narrow. Therefore, exceeding the upper limit value of condition expression (15) is not preferable.

In a case of falling below a lower limit value of conditional expression (15), it is not possible to achieve an adequate effect of increase in magnification. Moreover, since the height of a light ray at the optical element becomes high, the optical system becomes large in size. Therefore, falling below the lower limit value of conditional expression (15) is not preferable.

In the optical system for stereoscopic vision of the present embodiment, it is preferable that the following conditional expression (16) be satisfied:

$$0.004 < MG1Gn/MG1Gf < 0.2 \quad (16)$$

where,

MG1Gn denotes the lateral magnification of the first lens unit in the first optical system and the lateral magnification of the first lens unit in the second optical system at the time of focusing to the near point, and MG1Gf denotes the lateral magnification of the first lens unit in the first optical system and the lateral magnification of the first lens unit in the second optical system at the time of focusing to the far point.

In a case of exceeding an upper limit value of conditional expression (16), either an adequate amount of movement of the third lens unit has to be secured or the focusing sensitivity of the third lens unit has to be raised. When the amount of movement of the third lens unit is made large, correction of an off-axis aberration, particularly, correction of the curvature of field becomes difficult. When the focusing sensitivity of the third lens unit is raised, sensitivity of resolution degradation due to a position error also becomes high. Therefore, exceeding the upper limit value of conditional expression (16) is not preferable.

In a case of falling below a lower limit value of conditional expression (16), in the first optical system, it is not possible to achieve an adequate effect of increase in magnification and an effect of adjustment of the stereoscopic effect by the movement of the first entrance pupil at the time of focusing from the far point to the near point. Similar is true for the second optical system. Therefore, falling below the lower limit value of conditional expression (16) is not preferable.

In the optical system for stereoscopic vision of the present embodiment, it is preferable that the first lens unit in the first optical system and the first lens unit in the second optical system are integrated.

When a shift occurs between a position of the first lens unit of the first optical system and a position of the first lens unit of the second optical system, a vertical shift occurs between an image formed by the first optical system and an image formed by the second optical system. When the two first lens units are integrated, it is possible to make an amount of the vertical shift small. The two first lens units may be integrated by a method such as a method of gluing or a method of integrated molding.

In the optical system for stereoscopic vision of the present embodiment, it is preferable that the following conditional expression (17) be satisfied:

$$0.4 < (a \tan(IH/FLf)/a \tan(IH/FLn))/(\theta f/\theta n) < 0.85 \quad (17)$$

where $\theta f$ denotes a half angle of view at the time focusing to the far point, $\theta n$ denotes a half angle of view at the time of focusing to the near point, FLf denotes the focal length of the first optical system and the focal length of the second optical system at the time of focusing to the far point, FLn denotes the focal length of the first optical system and the focal length of the second optical system at the time of focusing to the near point, and IH denotes the maximum image height.

Conditional expression (17) is a conditional expression related to the angle of view at the time of focusing to the far point and the angle of view at the time of focusing to the near point. The angle of view at the time of focusing to the far point and the angle of view at the time of focusing to the near point include an angle of view calculated from the focal length and the image height, and a practical angle of view respectively. In conditional expression (17), for ratio of the angle of view at the time of focusing to the far point and the angle of view at the time of focusing to the near point, the angle of view calculated from the focal length and the image height, and the practical angle of view are compared.

In a case of exceeding an upper limit value of conditional expression (17), due to distortion, the vertical shift in an image of the first optical system and an image of the second optical system occur largely. In this case, even the stereoscopic image becomes a stereoscopic image with the vertical shift. Therefore, exceeding the upper limit value of conditional expression (17) is not preferable.

In a case of falling below a lower limit value of conditional expression (17), the stereoscopic image is a stereoscopic image in which a peripheral portion has protruded toward the observer. Therefore, falling below the lower limit value of conditional expression (17) is not preferable.

An image pickup apparatus of the present embodiment includes an optical system and an imager which has an image pickup surface and which converts an image formed on the image pickup surface by the optical system to an electric signal, and the optical system is the abovementioned optical system for stereoscopic vision.

According to the image pickup apparatus of the present embodiment, in spite of having a small size, it is possible to acquire an image in which an appropriate stereoscopic effect can be obtained at the time of viewing the object stereoscopically, even when the object distance is short. As a result, it is possible to carry out stereoscopic vision with little fatigue, even when the object distance is short For each conditional expression, the lower limit value and the upper limit value may be changed as shown below. Changing the upper limit value and the lower limit value as given below is favorable, as the effect of each conditional expression will be even more assured.

For conditional expression (1), it is preferable to make the lower limit value either −0.05 or −0.03, and it is preferable to make the upper limit value either 0.05 or 0.03.

For conditional expression (2), it is preferable to make the lower limit value either 0.15 or 0.20, and it is preferable to make the upper limit value either 0.60 or 0.40.

For conditional expression (3), it is preferable to make the lower limit value either 6.00 or 7.00, and it is preferable to make the upper limit value either 20.00 or 15.00.

For conditional expression (4), it is preferable to make the lower limit value either 0.06 or 0.07, and it is preferable to make the upper limit value either 0.20 or 0.15.

For conditional expression (5), it is preferable to make the lower limit value either 1.00 or 1.50, and it is preferable to make the upper limit value either 5.00 or 3.00.

For conditional expression (6), it is preferable to make the lower limit value either 0.50 or 0.60, and it is preferable to make the upper limit value either 1.00 or 0.95.

For conditional expression (7), it is preferable to make the lower limit value either 0.06 or 0.08, and it is preferable to make the upper limit value either 0.17 or 0.15.

For conditional expression (8), it is preferable to make the lower limit value either 1.10 or 1.20, and it is preferable to make the upper limit value either 1.80 or1.70.

For conditional expression (9), it is preferable to make the lower limit value either −0.04 or −0.03, and it is preferable to make the upper limit value either 0.04 or 0.02.

For conditional expression (10), it is preferable to make the lower limit value either −2.40 or −2.30, and it is preferable to make the upper limit value either −1.30 or −1.50.

For conditional expression (11), it is preferable to make the lower limit value either 1.70 or 2.00, and it is preferable to make the upper limit value either 5.00 or 4.50.

For conditional expression (12), it is preferable to make the lower limit value either −8.00 or −6.00, and it is preferable to make the upper limit value either 15.00 or 10.00.

For conditional expression (13), it is preferable to make the lower limit value either 3.00 or 3.50, and it is preferable to make the upper limit value either 20.00 or 16.00.

For conditional expression (14), it is preferable to make the lower limit value either 0.13 or 0.15, and it is preferable to make the upper limit value either 0.35 or 0.28.

For conditional expression (15), it preferable to make the lower limit value either 3.50 or 4.50, and it is preferable to make the upper limit value either 10.00 or 9.00.

For conditional expression (16), it is preferable to make the lower limit value either 0.005 or 0.006, and it is preferable to make the upper limit value either 0.15 or 0.10.

For conditional expression (17), it is preferable to make the lower limit value either 0.50 or 0.60, and it is preferable to make the upper limit value either 0.80 or 0.75.

Examples of optical systems for stereoscopic vision will be described below in detail by referring to the accompanying diagrams. However, the present disclosure is not restricted to the examples described below.

Lens cross-sectional views of examples and modified examples of the optical system for stereoscopic vision will be described below. FIG. 2, FIG. 3, FIG. 4, FIG. 5, FIG. 6, FIG. 7, FIG. 8, FIG. 9, FIG. 10, and FIG. 11 show lens cross-sectional views at the time of focusing to the far point. In the examples and the modified examples, the first optical system and the second optical system are the same.

Aberrations of examples will be described below.

FIG. 12A, FIG. 13A, FIG. 14A, FIG. 15A, FIG. 16A, FIG. 17A, FIG. 18A, FIG. 19A, FIG. 20A, FIG. 21A, FIG. 22A, and FIG. 23A shows an astigmatism.

FIG. 12B, FIG. 13B, FIG. 14B, FIG. 15B, FIG. 16B, FIG. 17B, FIG. 18B, FIG. 19B, FIG. 20B, FIG. 21B, FIG. 22B, and FIG. 23B show a distortion.

FIG. 12C, FIG. 12D, FIG. 12E, FIG. 12F, FIG. 12G, FIG. 12H, FIG. 12I, FIG. 12J, FIG. 13C, FIG. 13D, FIG. 13E, FIG. 13F, FIG. 13G, FIG. 13H, FIG. 13I, FIG. 13J, FIG. 14C, FIG. 14D, FIG. 14E, FIG. 14F, FIG. 14G, FIG. 14H, FIG. 14I, FIG. 14J, FIG. 15C, FIG. 15D, FIG. 15E, FIG. 15F, FIG. 15G, FIG. 15H, FIG. 15I, FIG. 15J, FIG. 16C, FIG. 16D, FIG. 16E, FIG. 16F, FIG. 16G, FIG. 16H, FIG. 16I, FIG. 16J, FIG. 17C, FIG. 17D, FIG. 17E, FIG. 17F, FIG. 17G, FIG. 17H, FIG. 17I, FIG. 17J, FIG. 18C, FIG. 18D, FIG. 18E, FIG. 18F, FIG. 18G, FIG. 18H, FIG. 18I, FIG. 18J, FIG. 19C, FIG. 19D, FIG. 19E, FIG. 19F, FIG. 19G, FIG. 19H, FIG. 19I, and FIG. 19J show a transverse aberration.

FIG. 20C, FIG. 20D, FIG. 20E, FIG. 20F, FIG. 20G, FIG. 20H, FIG. 20I, FIG. 20J, FIG. 21C, FIG. 21D, FIG. 21E, FIG. 21F, FIG. 21G, FIG. 21H, FIG. 21I, FIG. 21J, FIG. 22C, FIG. 22D, FIG. 22E, FIG. 22F, FIG. 22G, FIG. 22H, FIG. 22I, FIG. 22J, FIG. 23C, FIG. 23D, FIG. 23E, FIG. 23F, FIG. 23G, FIG. 23H, FIG. 23I, and FIG. 23J show a lateral aberration.

FIY denotes an image height.

In examples 1 to 6, there are aberration diagrams at the time of focusing to the near point and aberration diagrams at the time of focusing to the far point for each example. In the example 1, FIG. 12A to FIG. 12J are aberration diagrams at the time of focusing to the near point and FIG. 13A to FIG. 13J are aberration diagrams at the time of focusing to the far point. There are no aberration diagrams for modified examples 1 to 4.

In the transverse aberration, the maximum value of the horizontal axis is ±20 μm. A vertical axis is normalized by an entrance-pupil diameter. Ta denotes a tangential direction and Sa denotes a sagittal direction. IH0 denotes an axial, IH0.5 denotes 0.5 times of the maximum image height, IH0.7 denotes 0.7 times of the maximum image height, and IH1.0 denotes 1.0 times of the maximum image height.

An optical system for stereoscopic vision of the example 1 includes in order from an object side, a planoconcave negative lens L1, a biconcave negative lens L2, a biconvex positive lens L3, a positive meniscus lens L4 having a convex surface directed toward an image side, a biconvex positive lens L5, a biconvex positive lens L6, a negative meniscus lens L7 having a convex surface directed toward the object side, a biconvex positive lens L8, a biconcave negative lens L9, and a biconvex positive lens L10.

The biconcave negative lens L2 and the biconvex positive lens L3 are cemented. The biconcave negative lens L9 and the biconvex positive lens L10 are cemented.

An aperture stop S is disposed between the biconvex positive lens L5 and the biconvex positive lens L6. A cover glass C1 is disposed on the object side of the planoconcave negative lens L1. The cover glass C1 is the optical element disposed nearest to an object. A cover glass C2 is disposed on the image side of the biconvex positive lens L10.

The planoconcave negative lens L1 of the first optical system and the planoconcave negative lens L1 of the second optical system are integrated. The cover glass C1 is one plane parallel plate. The cover glass C1 is positioned to intersect both an optical axis of the first optical system and an optical axis of the second optical system.

At the time of focusing from a far point to a near point, the planoconcave negative lens L1 and the negative meniscus lens L7 move together toward the image side.

An aspheric surface is provided to an image-side surface of the planoconcave negative lens L1.

An optical system for stereoscopic vision of the example 2 includes in order from an object side, a planoconcave negative lens L1, a biconcave negative lens L2, a biconvex positive lens L3, a negative meniscus lens L4 having a convex surface directed toward an image side, a positive meniscus lens L5 having a convex surface directed toward the image side, a biconvex positive lens L6, a negative meniscus lens L7 having a convex surface directed toward the image side, a positive meniscus lens L8 having a convex surface directed toward the image side, a negative meniscus lens L9 having a convex surface directed toward the object side, and a biconvex positive lens L10.

The biconcave negative lens L2 and the biconvex positive lens L3 are cemented. The negative meniscus lens L9 and the biconvex positive lens L10 are cemented.

An aperture stop S is disposed between the biconvex positive lens L6 and the negative meniscus lens L7. A cover glass C1 is disposed on the object side of the planoconcave negative lens L1. The cover glass C1 is the optical element disposed nearest to an object. A cover glass C2 is disposed on the image side of the biconvex positive lens L10.

The planoconcave negative lens L1 of the first optical system and the planoconcave negative lens L1 of the second optical system are integrated. The cover glass C1 is one plane parallel plate. The cover glass C1 is positioned to intersect both an optical axis of the first optical system and an optical axis of the second optical system.

At the time of focusing from a far point to a near point, the planoconcave negative lens L1 moves toward the image side and the positive meniscus lens L8 moves toward the object side.

An aspheric surface is provided to an image-side surface of the planoconcave negative lens L1.

An optical system for stereoscopic vision of the example 3 includes in order from an object side, a planoconcave negative lens L1, a biconcave negative lens L2, a biconvex positive lens L3, a positive meniscus lens L4 having a convex surface directed toward an image side, a biconvex positive lens L5, a negative meniscus lens L6 having a convex surface directed toward the object side, a positive meniscus lens L7 having a convex surface directed toward the object side, a biconvex positive lens L8, a biconcave negative lens L9, a biconvex positive lens L10, and a positive meniscus lens L11 having a convex surface directed toward the image side.

The biconcave negative lens L2 and the biconvex positive lens L3 are cemented. The biconvex positive lens L8 and the biconcave negative lens L9 are cemented.

An aperture stop S is disposed between the biconvex positive lens L5 and the negative meniscus lens L6. A cover glass C1 is disposed on the object side of the planoconcave negative lens L1. The cover glass C1 is the optical element disposed nearest to an object. A cover glass C2 is disposed on the image side of the positive meniscus lens L11.

The planoconcave negative lens L1 of the first optical system and the planoconcave negative lens L1 of the second optical system are integrated. The cover glass C1 is one plane parallel plate. The cover glass C1 is positioned to intersect both an optical axis of the first optical system and an optical axis of the second optical system.

At the time of focusing from a far point to a near point, the planoconcave negative lens L1 and the negative meniscus lens L6 move together toward the image side.

An aspheric surface is provided to a total of six surfaces which are an image-side surface of the planoconcave negative lens L1, an object-side surface of the biconcave negative lens L2, both surfaces of the positive meniscus lens L7, an object-side surface of the biconvex positive lens L10, and an image-side surface of the positive meniscus lens L11.

An optical system for stereoscopic vision of the example 4 includes in order from an object side, a planoconcave negative lens L1, a biconcave negative lens L2, a biconvex positive lens L3, a positive meniscus lens L4 having a convex surface directed toward an image side, a biconvex positive lens L5, a biconvex positive lens L6, a negative meniscus lens L7 having a convex surface directed toward the object side, a biconvex positive lens L8, a biconcave negative lens L9, a biconvex positive lens L10, and a positive meniscus lens L11 having a convex surface directed toward the image side.

The biconcave negative lens L2 and the biconvex positive lens L3 are cemented. The biconcave negative lens L9 and the biconvex positive lens L10 are cemented.

An aperture stop S is disposed between the biconvex positive lens L5 and the biconvex positive lens L6. A cover glass C1 is disposed on the object side of the planoconcave negative lens L1. The cover glass C1 is the optical element disposed nearest to an object. A cover glass C2 is disposed on the image side of the positive meniscus lens L11.

The planoconcave negative lens L1 of the first optical system and the planoconcave negative lens L1 of the second optical system are integrated. The cover glass C1 is one plane parallel plate. The cover glass C1 is positioned to intersect both an optical axis of the first optical system and an optical axis of the second optical system.

At the time of focusing from a far point to a near point, the planoconcave negative lens L1 and the negative meniscus lens L7 move together toward the image side.

An aspheric surface is provided to a total of five surfaces which are an image-side surface of the planoconcave negative lens L1, both surfaces of the negative meniscus lens L7, and both surfaces of the positive meniscus lens L11.

An optical system for stereoscopic vision of the example 5 includes in order from an object side, a planoconcave negative lens L1, a negative meniscus lens L2 having a convex surface directed toward the object side, a biconcave negative lens L3, a biconvex positive lens L4, a positive meniscus lens L5 having a convex surface directed toward an image side, a positive meniscus lens L6 having a convex surface directed toward the image side, a biconvex positive lens L7, a negative meniscus lens L8 having a convex surface directed toward the object side, a biconvex positive lens L9, a biconcave negative lens L10, a biconvex positive lens L11, and a negative meniscus lens L12 having a convex surface directed toward the image side.

The biconcave negative lens L3 and the biconvex positive lens L4 are cemented. The biconcave negative lens L10 and the biconvex positive lens L11 are cemented.

An aperture stop S is disposed between the positive meniscus lens L6 and the biconvex positive lens L7. A cover glass C1 is disposed on the object side of the planoconcave negative lens L1. The cover glass C1 is the optical element disposed nearest to an object. A cover glass C2 is disposed on the image side of the negative meniscus lens L12.

The planoconcave negative lens L1 of the first optical system and the planoconcave negative lens L1 of the second optical system are integrated. The cover glass C1 is one plane and parallel plate. The cover glass C1 is positioned to intersect both an optical axis of the first optical system and an optical axis of the second optical system.

At the time of focusing from a far point to a near point, the planoconcave negative lens L1 and the negative meniscus lens L8 move together toward the image side.

An aspheric surface is provided to a total of six surfaces which are an image-side surface of the planoconcave negative lens L1, an image-side surface of the negative meniscus lens L2, both surfaces of the biconvex positive lens L7, and both surfaces of the biconvex positive lens L11.

An optical system for stereoscopic vision of the example 6 includes in order from an object side, a planoconcave negative lens L1, a biconcave negative lens L2, a biconvex positive lens L3, a positive meniscus lens L4 having a convex surface directed toward an image side, a biconvex positive lens L5, a biconvex positive lens L6, a negative meniscus lens L7 having a convex surface directed toward the object side, a biconvex positive lens L8, a biconcave negative lens L9, a biconvex positive lens L10, and a positive meniscus lens L11 having a convex surfaced directed toward the image side.

The biconcave negative lens L2 and the biconvex positive lens L3 are cemented. The biconcave negative lens L9 and the biconvex positive lens L10 are cemented.

An aperture stop S is disposed between the biconvex positive lens L5 and the biconvex positive lens L6. A cover glass C1 is disposed on the object side of the planoconcave negative lens L1. The cover glass C1 is the optical element disposed nearest to an object. A cover glass C2 is disposed on the image side of the positive meniscus lens L11.

The planoconcave negative lens L1 of the first optical system and the planoconcave negative lens L1 of the second optical system are integrated. The cover glass C1 is one plane parallel plate. The cover glass C1 is disposed to intersect both an optical axis of the first optical system and an optical axis of the second optical system.

At the time of focusing from a far point to a near point, the planoconcave negative lens L1 and the negative meniscus lens L7 move together toward the image side.

An aspheric surface is provided to a total of five surfaces which are an image-side surface of the planoconcave negative lens L1, both surfaces of the negative meniscus lens L7, and both surfaces of the positive meniscus lens L11.

An optical system for stereoscopic vision of the modified example 1 is an optical system in which the cover glass in the optical system for stereoscopic vision of the example 1 is replaced by another cover glass. In the optical system for stereoscopic vision of the example 1, both the surfaces of the cover glass C1 are flat surfaces. Whereas, in the optical system for stereoscopic vision of the modified example 1, an object-side surface of a cover glass C1 is a spherical surface and an image-side surface of the cover glass C1 is a flat surface. A radius of curvature of the object-side surface is 100 mm. In the optical system for stereoscopic vision of the modified example 1, the cover glass C1 is a planoconvex positive lens of which an object-side is a convex surface.

An optical system for stereoscopic vision of the modified example 2 is an optical system in which the cover glass in the optical system for stereoscopic vision of the example 1 is replaced by another cover glass. In the optical system for stereoscopic vision of the modified example 2, an object-side surface of a cover glass C1 is a flat surface and an image-side surface of the cover glass C1 is a spherical surface. A radius of curvature of the image-side surface is 50 mm. In the optical system for stereoscopic vision of the modified example 2, the cover glass C1 is a planoconcave negative lens of which an object side is a flat surface.

An optical system for stereoscopic vision of the modified example 3 is an optical system in which the cover glass in the optical system for stereoscopic vision of the example 1 is replaced by another cover glass. In the optical system for stereoscopic vision of the modified example 3, both an object-side surface and an image-side surface of a cover glass C1 are spherical surfaces. Both a radius of curvature of the object-side surface and a radius of curvature of the image-side surface are 100 mm.

An optical system for stereoscopic vision of the modified example 4 is an optical system in which an optical filter is disposed in the optical system for stereoscopic vision of the example 1. In the optical system for stereoscopic vision of the modified example 4, an optical filter F is disposed between a cover glass C1 and a planoconcave negative lens L1.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens, and * denotes an aspherical surface.

Moreover, a shape of an aspherical surface is defined by the following expression, where the direction of the optical axis is represented by z, the direction orthogonal to the optical axis is represented by y, a conical coefficient is represented by K, aspherical surface coefficients are represented by A4, A6, A8, A10, A12 . . . .

$$Z=(y^2/r)/[1+\{1-(1+k)(y/r)^2\}^{1/2}]+A4\,y^4+A6\,y^6+A8\,y^8+A10\,y^{10}+A12\,y^{12}+\ldots$$

Further, in the aspherical surface coefficients, 'e–n' (where, n is an integral number) indicates '$10^{-n}$'. Moreover, these symbols are commonly used in the following numerical data for each example.

EXAMPLE 1

| Unit mm | | | | |
|---|---|---|---|---|
| Surface data | | | | |
| Surface no. | r | d | nd | vd |
| Object plane | ∞ | | | |
| 1 | ∞ | 0.35 | 1.88300 | 40.77 |
| 2 | ∞ | Variable | | |
| 3 | ∞ | 0.53 | 1.88300 | 40.77 |
| 4* | 1.366 | Variable | | |
| 5 | −4.457 | 0.50 | 1.88300 | 40.77 |
| 6 | 3.332 | 1.17 | 1.48749 | 70.24 |
| 7 | −2.537 | 0.23 | | |
| 8 | −10.043 | 0.91 | 1.48749 | 70.24 |
| 9 | −3.543 | 0.09 | | |
| 10 | 110.267 | 0.97 | 1.77250 | 49.60 |
| 11 | −5.487 | 0.09 | | |
| 12(Stop) | ∞ | 0.08 | | |
| 13 | 3.798 | 0.87 | 1.49700 | 81.61 |
| 14 | −13.739 | Variable | | |
| 15 | 3.330 | 0.58 | 1.77250 | 49.60 |
| 16 | 1.398 | Variable | | |
| 17 | 4.700 | 1.00 | 1.80400 | 46.58 |
| 18 | −2.517 | 0.17 | | |
| 19 | −3.145 | 0.50 | 1.92286 | 18.90 |
| 20 | 3.179 | 1.72 | 1.77250 | 49.60 |
| 21 | −4.557 | 0.08 | | |
| 22 | ∞ | 1.25 | 1.51009 | 63.64 |
| 23 | ∞ | 0 | | |
| Image plane | ∞ | | | |

| Aspherical surface data | |
|---|---|
| 4th surface | |
| k = 0.190 | |

| Various data | | |
|---|---|---|
| Focusing Point | Near Point | Far Point |
| Object distance | 3.5 | 35.0 |
| d2 | 1.66 | 0.15 |
| d4 | 0.75 | 2.25 |
| d14 | 1.31 | 0.23 |
| d16 | 0.33 | 1.41 |

EXAMPLE 2

| Unit mm | | | | |
|---|---|---|---|---|
| Surface data | | | | |
| Surface no. | r | d | nd | vd |
| Object plane | ∞ | | | |
| 1 | ∞ | 0.35 | 1.88300 | 40.77 |
| 2 | ∞ | Variable | | |
| 3 | ∞ | 0.54 | 1.88300 | 40.77 |
| 4* | 1.463 | Variable | | |
| 5 | −33.547 | 0.51 | 1.88300 | 40.77 |
| 6 | 3.402 | 1.29 | 1.48749 | 70.24 |
| 7 | −2.066 | 0.09 | | |
| 8 | −2.639 | 1.71 | 1.43385 | 95.23 |
| 9 | −4.327 | 1.49 | | |
| 10 | −7.334 | 0.90 | 1.77250 | 49.60 |
| 11 | −3.793 | 0.09 | | |
| 12 | 9.069 | 0.90 | 1.49700 | 81.61 |
| 13 | −2.914 | 0.09 | | |
| 14(Stop) | ∞ | 0.26 | | |
| 15 | −2.267 | 0.60 | 1.77250 | 49.60 |
| 16 | −4.841 | Variable | | |
| 17 | −7.360 | 0.85 | 1.80400 | 46.58 |
| 18 | −3.769 | Variable | | |
| 19 | 10.448 | 0.51 | 1.92286 | 18.90 |
| 20 | 2.041 | 1.19 | 1.77250 | 49.60 |
| 21 | −14.760 | 0.78 | | |
| 22 | ∞ | 1.27 | 1.51009 | 63.64 |
| 23 | ∞ | 0 | | |
| Image plane | ∞ | | | |

-continued

| Unit mm | | |
|---|---|---|
| Aspherical surface data | | |
| 4th surface | | |
| k = 0.200 | | |
| Various data | | |
| Focusing Point | Near Point | Far Point |
| Object distance | 3.4 | 25.0 |
| d2 | 1.70 | 0.15 |
| d4 | 0.85 | 2.38 |
| d16 | 0.82 | 2.58 |
| d18 | 2.11 | 0.35 |

EXAMPLE 3

| Unit mm | | | | |
|---|---|---|---|---|
| Surface data | | | | |
| Surface no. | r | d | nd | vd |
| Object plane | ∞ | | | |
| 1 | ∞ | 0.35 | 1.88300 | 40.77 |
| 2 | ∞ | Variable | | |
| 3 | ∞ | 0.49 | 1.88300 | 40.77 |
| 4* | 1.493 | Variable | | |
| 5* | −2.666 | 0.41 | 1.88300 | 40.77 |
| 6 | 1.955 | 1.09 | 1.67790 | 55.34 |
| 7 | −2.556 | 0.10 | | |
| 8 | −7.623 | 0.81 | 1.67790 | 55.34 |
| 9 | −3.129 | 0.08 | | |
| 10 | 9.042 | 0.90 | 1.65160 | 58.55 |
| 11 | −3.948 | 0.08 | | |
| 12(Stop) | ∞ | Variable | | |
| 13 | 2.502 | 0.41 | 1.77250 | 49.60 |
| 14 | 1.449 | Variable | | |
| 15* | 4.887 | 0.70 | 1.88300 | 40.77 |
| 16* | 10.269 | 0.13 | | |
| 17 | 6.686 | 0.90 | 1.72916 | 54.68 |
| 18 | −3.258 | 0.41 | 1.92286 | 18.90 |
| 19 | 4.438 | 0.13 | | |
| 20* | 3.937 | 1.13 | 1.88300 | 40.77 |
| 21 | −7.381 | 0.10 | | |
| 22 | −7.654 | 0.81 | 1.88300 | 40.77 |
| 23* | −4.593 | 0.12 | | |
| 24 | ∞ | 1.00 | 1.51009 | 63.64 |
| 25 | ∞ | 0 | | |
| Image plane | ∞ | | | |

Aspherical surface data

4th surface k = 0.516
5th surface k = 0.000
A4 = −2.19676e−02, A6 = −3.88873e−03
15th surface k = 0.000
A4 = −5.78515e−03
16th surface k = 0.000
A4 = −2.89686e−02
20th surface k = 0.000
A4 = −1.55362e−02, A6 = −5.29948e−03

-continued

| Unit mm | | |
|---|---|---|
| 23rd surface | | |
| k = 0.000 | | |
| A4 = −1.22317e−02, A6 = −1.36559e−03 | | |
| Various data | | |
| Focusing Point | Near Point | Far Point |
| Object distance | 3.2 | 33.0 |
| d2 | 1.79 | 0.15 |
| d4 | 1.03 | 2.66 |
| d12 | 1.87 | 0.24 |
| d14 | 0.33 | 1.96 |

EXAMPLE 4

| Unit mm | | | | |
|---|---|---|---|---|
| Surface data | | | | |
| Surface no. | r | d | nd | vd |
| Object plane | ∞ | | | |
| 1 | ∞ | 0.40 | 1.88300 | 40.77 |
| 2 | ∞ | Variable | | |
| 3 | ∞ | 0.67 | 1.88300 | 40.77 |
| 4* | 1.781 | Variable | | |
| 5 | −4.778 | 0.47 | 1.88300 | 40.77 |
| 6 | 2.026 | 1.32 | 1.60311 | 60.64 |
| 7 | −2.616 | 0.08 | | |
| 8 | −3.919 | 1.00 | 1.48749 | 70.24 |
| 9 | −3.105 | 0.08 | | |
| 10 | 41.122 | 1.09 | 1.74320 | 49.30 |
| 11 | −6.197 | 0.08 | | |
| 12(Stop) | ∞ | Variable | | |
| 13 | 3.648 | 0.88 | 1.74320 | 49.30 |
| 14 | −22.644 | Variable | | |
| 15* | 7.023 | 0.50 | 1.88300 | 40.77 |
| 16* | 1.527 | Variable | | |
| 17 | 6.782 | 1.17 | 1.88300 | 40.77 |
| 18 | −2.456 | 0.17 | | |
| 19 | −3.688 | 0.48 | 1.92286 | 18.90 |
| 20 | 2.696 | 1.03 | 1.74320 | 49.30 |
| 21 | −4.345 | 0.13 | | |
| 22* | −6.172 | 0.87 | 1.88300 | 40.77 |
| 23* | −5.281 | 0.19 | | |
| 24 | ∞ | 1.30 | 1.51009 | 63.64 |
| 25 | ∞ | 0 | | |
| Image plane | ∞ | | | |

Aspherical surface data

4th surface k = 0.404
15th surface k = 0.000
A4 = −1.34664e−02
16th surface k = 0.000
A4 = −1.29253e−02
22nd surface k = 0.000
A4 = 4.81010e−03
23rd surface k = 0.000
A4 = 5.04437e−03

-continued

Unit mm

Various data

| Focusing Point | Near Point | Far Point |
|---|---|---|
| Object distance | 3.3 | 34.0 |
| d2 | 2.45 | 0.25 |
| d4 | 0.98 | 3.18 |
| d14 | 0.84 | 0.28 |
| d16 | 0.43 | 0.99 |

EXAMPLE 5

Unit mm

Surface data

| Surface no. | r | d | nd | vd |
|---|---|---|---|---|
| Object plane | ∞ | | | |
| 1 | ∞ | 0.35 | 1.88300 | 40.77 |
| 2 | ∞ | Variable | | |
| 3 | ∞ | 0.67 | 1.88300 | 40.77 |
| 4* | 1.780 | Variable | | |
| 5 | 1.816 | 0.50 | 1.55000 | 53.00 |
| 6* | 1.482 | 2.33 | | |
| 7 | −5.414 | 0.47 | 1.88300 | 40.77 |
| 8 | 2.013 | 1.32 | 1.60311 | 60.64 |
| 9 | −2.628 | 0.08 | | |
| 10 | −3.814 | 1.00 | 1.48749 | 70.24 |
| 11 | −2.990 | 0.08 | | |
| 12 | −146.268 | 1.00 | 1.74320 | 49.30 |
| 13 | −4.706 | 0.08 | | |
| 14(Stop) | ∞ | 0.08 | | |
| 15 | 3.870 | 0.89 | 1.74320 | 49.30 |
| 16 | −23.280 | Variable | | |
| 17* | 6.483 | 0.50 | 1.88300 | 40.77 |
| 18* | 1.607 | Variable | | |
| 19 | 6.892 | 1.17 | 1.88300 | 40.77 |
| 20 | −2.715 | 0.17 | | |
| 21 | −3.674 | 0.49 | 1.92286 | 18.90 |
| 22 | 2.432 | 0.71 | 1.74320 | 49.30 |
| 23 | −3.335 | 0.13 | | |
| 24* | −3.956 | 0.67 | 1.88300 | 40.77 |
| 25* | −4.707 | 0.16 | | |
| 26 | ∞ | 1.35 | 1.51009 | 63.64 |
| 27 | ∞ | 0 | | |
| Image plane | ∞ | | | |

Aspherical surface data

4th surface k = 0.399
6th surface k = 0.000
A4 = −9.85274e−03
17th surface k = 0.000
A4 = −3.10322e−02
18th surface k = 0.000
A4 = −4.88512e−02
24th surface k = 0.000
A4 = −2.89502e−02

-continued

Unit mm

25th surface k = 0.000
A4 = −2.87267e−02

Various data

| Focusing Point | Near Point | Far Point |
|---|---|---|
| Object distance | 3.4 | 34.0 |
| d2 | 1.93 | 0.25 |
| d4 | 0.65 | 2.33 |
| d16 | 0.86 | 0.29 |
| d18 | 0.44 | 1.01 |

EXAMPLE 6

Unit mm

Surface data

| Surface no. | r | d | nd | vd |
|---|---|---|---|---|
| Object plane | ∞ | | | |
| 1 | ∞ | 0.35 | 1.88300 | 40.77 |
| 2 | ∞ | Variable | | |
| 3 | ∞ | 0.67 | 1.88300 | 40.77 |
| 4* | 1.792 | Variable | | |
| 5 | −4.783 | 0.47 | 1.88300 | 40.77 |
| 6 | 2.027 | 1.32 | 1.60311 | 60.64 |
| 7 | −2.617 | 0.08 | | |
| 8 | −3.923 | 1.00 | 1.48749 | 70.24 |
| 9 | −3.107 | 0.08 | | |
| 10 | 40.599 | 1.08 | 1.74320 | 49.30 |
| 11 | −6.276 | 0.08 | | |
| 12(Stop) | ∞ | 0.08 | | |
| 13 | 3.630 | 0.88 | 1.74320 | 49.30 |
| 14 | −22.682 | Variable | | |
| 15* | 7.034 | 0.50 | 1.88300 | 40.77 |
| 16* | 1.529 | Variable | | |
| 17 | 6.839 | 1.17 | 1.88300 | 40.77 |
| 18 | −2.449 | 0.17 | | |
| 19 | −3.678 | 0.48 | 1.92286 | 18.90 |
| 20 | 2.647 | 1.03 | 1.74320 | 49.30 |
| 21 | −4.307 | 0.13 | | |
| 22* | −6.236 | 0.87 | 1.88300 | 40.77 |
| 23* | −5.235 | 0.17 | | |
| 24 | ∞ | 1.33 | 1.51009 | 63.64 |
| 25 | ∞ | 0 | | |
| Image plane | ∞ | | | |

Aspherical surface data

4th surface k = 0.229
15th surface k = 0.000
A4 = −1.60647e−02
16th surface k = 0.000
A4 = −1.81454e−02
22nd surface k = 0.000
A4 = 1.62081e−02
23rd surface k = 0.000
A4 = 3.24061e−02

-continued

Unit mm

Various data

| Focusing Point | Near Point | Far Point |
|---|---|---|
| Object distance | 3.5 | 30.0 |
| d2 | 2.45 | 0.25 |
| d4 | 0.98 | 3.18 |
| d14 | 0.84 | 0.28 |
| d16 | 0.43 | 0.99 |

Next, values of conditional expressions in each example are given below.

| | | Example 1 | Example 2 | Example 3 |
|---|---|---|---|---|
| (1) | FL1m/FLc | 0.00 | 0.00 | 0.00 |
| (2) | atan(De/Loben) − atan(De/Lobef) | 0.30 | 0.27 | 0.34 |
| (3) | (Lnobf − Lnobn)/Dax | 11.99 | 7.71 | 9.71 |
| (4) | (Lc1mn − Lc1mf)/TTL | 0.10 | 0.08 | 0.11 |
| (5) | Lcef/IH | 1.87 | 2.06 | 1.97 |
| (6) | Lcef/De | 0.69 | 0.75 | 0.61 |
| (7) | Lcef/TTL | 0.11 | 0.10 | 0.12 |
| (8) | FLn/FLf | 1.51 | 1.23 | 1.65 |
| (9) | IH/FLc | 0.00 | 0.00 | 0.00 |
| (10) | FL1G/IH | −1.67 | −1.76 | −1.88 |
| (11) | FL2G/IH | 2.30 | 4.37 | 2.53 |
| (12) | FL3G/IH | −3.89 | 9.22 | −5.95 |
| (13) | FL4G/IH | 3.88 | 15.86 | 3.91 |
| (14) | (MG1Gf/MG1Gn)/ (MG3Gf/MG3Gn) | 0.18 | 0.18 | 0.18 |
| (15) | MGn/MGf | 8.71 | 4.94 | 8.96 |
| (16) | MG1Gn/MG1Gf | 0.012 | 0.090 | 0.017 |
| (17) | (atan(IH/FLf)/ atan(IH/FLn))/(θf/θn) | 0.65 | 0.69 | 0.61 |

| | | Example 4 | Example 5 | Example 6 |
|---|---|---|---|---|
| (1) | FL1m/FLc | 0.00 | 0.00 | 0.00 |
| (2) | atan(De/Loben) − atan(De/Lobef) | 0.25 | 0.27 | 0.26 |
| (3) | (Lnobf − Lnobn)/Dax | 11.88 | 11.57 | 9.00 |
| (4) | (Lc1mn − Lc1mf)/TTL | 0.13 | 0.11 | 0.13 |
| (5) | Lcef/IH | 2.53 | 2.82 | 2.49 |
| (6) | Lcef/De | 0.93 | 0.88 | 0.82 |
| (7) | Lcef/TTL | 0.13 | 0.14 | 0.13 |
| (8) | FLn/FLf | 1.63 | 1.50 | 1.63 |
| (9) | IH/FLc | 0.00 | 0.00 | 0.00 |
| (10) | FL1G/IH | −2.28 | −2.16 | −2.28 |
| (11) | FL2G/IH | 2.07 | 2.29 | 2.21 |
| (12) | FL3G/IH | −2.61 | −3.24 | −2.60 |
| (13) | FL4G/IH | 3.66 | 4.56 | 3.62 |
| (14) | (MG1Gf/MG1Gn)/ (MG3Gf/MG3Gn) | 0.22 | 0.20 | 0.25 |
| (15) | MGn/MGf | 8.13 | 7.94 | 7.05 |
| (16) | MG1Gn/MG1Gf | 0.007 | 0.010 | 0.009 |
| (17) | (atan(IH/FLf)/ atan(IH/FLn))/(θf/θn) | 0.64 | 0.70 | 0.72 |

Figure 24:
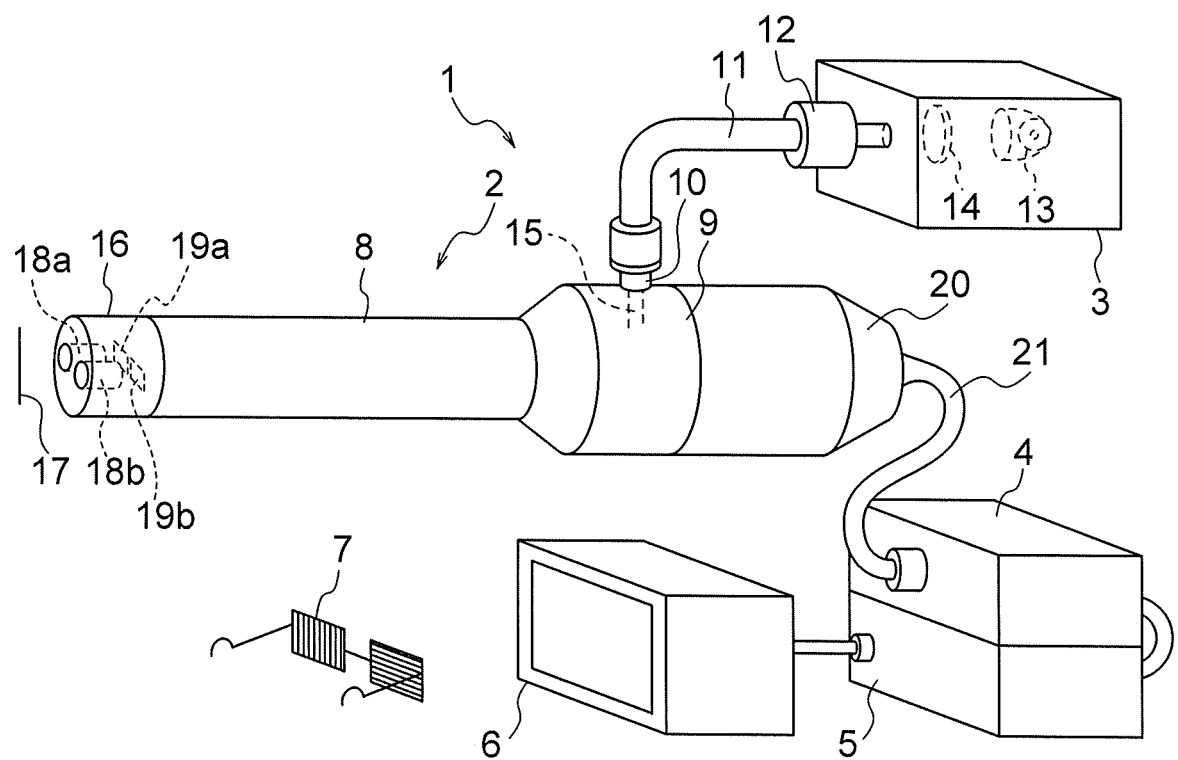
FIG. 24 is a diagram showing an image pickup apparatus of the present embodiment.

FIG. 24 is a diagram showing an image pickup apparatus of the present embodiment. The image pickup apparatus of the present embodiment is a stereoscopic-vision endoscope. A stereoscopic-vision endoscope 1 includes a body portion 2, a light-source unit 3, a camera control unit 4 (hereinafter, referred to as 'CCU 4'), a scan converter 5, a monitor 6, and shutter glasses 7.

The body portion 2 includes an insertion portion 8 and a holding portion 9. The insertion portion 8 is a portion to be inserted into a body cavity, and is formed by a hard jacket tube. The jacket tube is in the form of a circular tube, and is made of a metal such as stainless steel. In such manner, the stereoscopic-vision endoscope 1 is a rigid endoscope. The holding portion 9 is a portion to be held by an operator.

The holding portion 9 is provided with a light-guide tube 10. One end of a light-guide cable 11 is connected to the light-guide tube 10. The other end of the light-guide cable 11 is provided with a light-guide connector 12. The light-guide cable 11 is detachably connected to the holding portion 9 and the light-source unit 3.

The light-source unit 3 includes a lamp 13 and a lens 14. The lamp 13 generates illumination light such as white light. The lens 14 focuses the illumination light. The illumination light focused by the lens 14 is irradiated to an end surface of the light-guide connector 12. The illumination light irradiated to the end surface is transmitted to the body portion 2 by a light guide inside the light-guide cable 11.

The body portion 2 is provided with a light guide 15. The light guide 15 is bent inside the holding portion 9, and is passed through the insertion portion 8. The light guide 15 transmits the illumination light supplied from the light-guide cable 11 to a front-end surface which is fixed to a front-end portion 16 of the insertion portion 8. Accordingly, the illumination light is emerged frontward from the front-end surface.

Inside of the front-end portion 16, an optical system for stereoscopic vision of the present embodiment is disposed. The optical system for stereoscopic vision includes an objective optical system 18a and an objective optical system 18b.

An object 17 is illuminated by the illumination light. Light from the object 17 is incident on the objective optical system 18a and the objective optical system 18b. An optical image is formed at an image forming position of the objective optical system 18a. An optical image 19b is formed at an image forming position of the objective optical system 18b.

A first imager 19a is disposed at the image forming position of the objective optical system 18a. The optical image formed by the objective optical system 18a is captured by the first imager 19a. A second imager 19b is disposed at the image forming position of the objective optical system 18b. The optical image formed by the objective optical system 18b is captured by the first imager 19b.

One end of a signal cable 21 is connected to an output portion 20. The other end of the signal cable 21 is connected to the CCU 4. A signal which is output from the first imager 19a and a signal which is output from the second imager 19b are input to the CCU 4 via the signal cable 21.

In the CCU 4, signal processing is carried out on signals output from the first imager 19a and the second imager 19b. An image signal subjected to signal processing in the CCU 4 is input to the scan converter 5. In the scan converter 5, the signal output from the CCU 4 is converted to a video signal.

The video signal is input to the monitor 6. The monitor 6 displays the video signal that has been input. Two images having a parallax are displayed alternately on the monitor 6. The shutter glasses 7 have a shutter function. By using the shutter glasses 7, images displayed on the monitor 6 can be viewed stereoscopically.

According to the present embodiment, it is possible to provide a small-sized optical system for stereoscopic vision in which aberrations are corrected favorably and an appropriate inward angle can be achieved even when an object distance is short, and an image pickup apparatus using such optical system for stereoscopic vision.

As described heretofore, the present disclosure is suitable for a small-sized optical system for stereoscopic vision in which aberrations are corrected favorably and an appropriate inward angle can be achieved even when an object distance is short. Moreover, the present disclosure is suitable for a small-sized image pickup apparatus in which an appropriate stereoscopic effect can be obtained at the time of viewing an object stereoscopically, even when the object distance is short.

What is claimed is:

1. An optical system for stereoscopic vision, comprising:
a first optical system,
a second optical system, and
an optical element on an object side of the first optical system and the second optical system,
wherein:
each of the first optical system and the second optical system includes a stop and a plurality of lens units,
the plurality of lens units include a movable lens unit which moves at the time of focusing and a lens unit which is fixed at the time of focusing,
at least focusing to a near point and focusing to a far point is carried out by a movement of the movable lens unit,
at the time of focusing to the near point, both a first entrance pupil and a second entrance pupil are positioned on an image side of positions at the time of focusing to the far point, and
the following conditional expression (5) is satisfied:

$$0.5 < Lcef/IH < 10.0 \qquad (5)$$

where,
the first entrance pupil is an entrance pupil of the first optical system,
the second entrance pupil is an entrance pupil of the second optical system,
the near point is a point in a focusing range, positioned nearest to the optical system for stereoscopic vision,
the far point is a point in the focusing range, positioned farthest from the optical system for stereoscopic vision,
Lcef denotes a distance on an optical axis from an object-side surface of the optical element up to a position of the first entrance pupil at the time of focusing to the far point, and a distance on the optical axis from the object-side surface of the optical element up to a position of the second entrance pupil at the time of focusing to the far point, and
IH denotes the maximum image height.

2. An optical system for stereoscopic vision, comprising:
a first optical system,
a second optical system, and
an optical element,
wherein:
the first optical system and the second optical system are disposed on an image side of the optical element,
the optical element is positioned to intersect both an optical axis of the first optical system and an optical axis of the second optical system,
each of the first optical system and the second optical system includes a stop, two movable lens units which move at a time of focusing, and a lens unit which is fixed at the time of focusing,
the two movable lens units include, in order from the object side, a first movable lens unit and a second movable lens unit,
at least focusing to a near point and focusing to a far point is carried out by a movement of at least the second movable lens unit,
at the time of focusing from the far point to the near point, the first movable lens unit moves from the object side toward the image side, and
the following conditional expressions (1) and (4) are satisfied:

$$-0.1 < FL1m/FLc < 0.1 \qquad (1)$$

$$0.05 < (Lc1mn - Lc1mf)/TTL < 0.25 \qquad (4)$$

where,
FLc denotes a focal length of the optical element,
FL1m denotes a focal length of the first movable lens unit in the first optical system and a focal length of the first movable lens unit in the second optical system,
the near point is a point in a focusing range, positioned nearest to the optical system for stereoscopic vision,
the far point is a point in the focusing range, positioned farthest from the optical system for stereoscopic vision,
Lc1mn denotes a distance on an optical axis from an object-side surface of the optical element up to a lens surface positioned nearest to an object of the first movable lens unit in the first optical system at the time of focusing to the near point, and a distance on the optical axis from the object-side surface of the optical element up to a lens surface positioned nearest to the object of the first movable lens unit in the second optical system at the time of focusing to the near point,
Lc1mf denotes a distance on the optical axis from the object-side surface of the optical element up to the lens surface positioned nearest to the object of the first movable lens unit in the first optical system at the time of focusing to the far point, and a distance on the optical axis from the object-side surface of the optical element up to the lens surface positioned nearest to the object of the first movable lens unit in the second optical system at the time of focusing to the far point, and
TTL denotes a distance on the optical axis from the object-side surface of the optical element up to an image plane.

3. An optical system for stereoscopic vision, comprising:
a first optical system, and
a second optical system,
wherein:
each of the first optical system and the second optical system includes a stop and a movable lens unit which moves at the time of focusing,
at least focusing to a near point and focusing to a far point are carried out by a movement of the movable lens unit, and
a focus position is changed by moving the movable lens unit while satisfying the following conditional expression (2):

$$0.1 < a\tan(De/Loben) - a\tan(De/Lobef) < 0.8 \qquad (2)$$

where,
De denotes a distance between a center of a first entrance pupil and a center of a second entrance pupil,
Loben denotes a distance on an optical axis from a position of the near point up to a position of the first entrance pupil at the time of focusing to the near point and a distance on the optical axis from the position of the near point up to a position of the second entrance pupil at the time of focusing to the near point, and
Lobef denotes a distance on the optical axis from a position of the far point up to a position of the first entrance pupil at the time of focusing to the far point and a distance on the optical axis from the position of the far point up to a position of the second entrance pupil at the time of focusing to the far point, and here the first entrance pupil is an entrance pupil of the first optical system, the second entrance pupil is an entrance pupil of the second optical system, the near point is a point in a focusing range, positioned nearest to the optical system for stereoscopic vision, and the far point is a point in the focusing range, positioned farthest from the optical system for stereoscopic vision.

4. An optical system for stereoscopic vision, comprising:
a first optical system,
a second optical system, and
an optical element,
wherein:
the first optical system and the second optical system are disposed on an image side of the optical element,
each of the first optical system and the second optical system includes a stop and a lens unit having a negative refractive power,
at the time of focusing from a far point to a near point, the optical element is fixed, and the lens unit having a negative refractive power moves from the object side toward the image side as a movable lens unit, and
the following conditional expression (3) is satisfied:

$$5.0 < (Lnobf - Lnobn)/Dax < 50.0 \quad (3)$$

where,
Dax denotes a distance between an optical axis of the first optical system and an optical axis of the second optical system, Lnobf denotes a distance on an optical axis from a surface nearest to an object of the lens unit having a negative refractive power in the first optical system at the time of focusing to the far point up to a position of the far point, and a distance on the optical axis from a surface nearest to the object of the lens unit having a negative refractive power in the second optical system at the time of focusing to the far point up to the position of the far point, and Lnobn denotes a distance on the optical axis from the surface nearest to the object of the lens unit having a negative refractive power in the first optical system at the time of focusing to the near point up to a position of the near point, and a distance on the optical axis from the surface nearest to the object of the lens unit having a negative refractive power in the second optical system at the time of focusing to the near point up to the position of the near point, and here the near point is a point in a focusing range, positioned nearest to the optical system for stereoscopic vision, and the far point is a point in the focusing range, positioned farthest from the optical system for stereoscopic vision.

5. The optical system for stereoscopic vision according to claim 1, wherein the following conditional expression (6) is satisfied:

$$0.3 < Lcef/De < 2.0 \quad (6)$$

where,
De denotes a distance between a center of the first entrance pupil and a center of the second entrance pupil.

6. The optical system for stereoscopic vision according to claim 1, wherein the following conditional expression (7) is satisfied:

$$0.04 < Lcef/TTL < 0.2 \quad (7)$$

where,
TTL denotes a distance on the optical axis from the object-side surface of the optical element up to an image plane.

7. The optical system for stereoscopic vision according to claim 1, wherein the following conditional expression (8) is satisfied:

$$1.0 < FLn/FLf < 2.0 \quad (8)$$

where,
FLf denotes a focal length of the first optical system and a focal length of the second optical system, at the time of focusing to the far point, and
FLn denotes a focal length of the first optical system and a focal length of the second optical system, at the time of focusing to the near point.

8. The optical system for stereoscopic vision according to claim 1, wherein each of the first optical system and the second optical system includes, in order from the object side:
a first lens unit having a negative refractive power,
a second lens unit having a positive refractive power,
a third lens unit, and
a fourth lens unit.

9. The optical system for stereoscopic vision according to claim 2, wherein the optical element has a symmetrical shape with respect to a central axis which is positioned between the optical axis of the first optical system and the optical axis of the second optical system.

10. The optical system for stereoscopic vision according to claim 8, wherein the optical element has a symmetrical shape with respect to a central axis positioned between an optical axis of the first optical system and an optical axis of the second optical system.

11. The optical system for stereoscopic vision according to claim 8, wherein the optical element is fixed at the time of focusing.

12. The optical system for stereoscopic vision according to claim 8, wherein the optical element is a plane parallel plate.

13. The optical system for stereoscopic vision according to claim 2, wherein the first movable lens unit is a negative lens.

14. The optical system for stereoscopic vision according to claim 8, wherein the third lens unit moves at the time of focusing.

15. The optical system for stereoscopic vision according to claim 8, wherein the third lens unit has a negative refractive power and moves from the object side toward the image side at the time of focusing from the far point to the near point.

16. The optical system for stereoscopic vision according to claim 8, wherein the third lens unit has a positive refractive power and moves from the image side toward the object side at the time of focusing from the far point to the near point.

17. The optical system for stereoscopic vision according to claim 8, wherein the following conditional expression (9) is satisfied:

$$-0.1 < IH/FLc < 0.1 \quad (9)$$

where,
FLc denotes a focal length of the optical element.

18. The optical system for stereoscopic vision according to claim 8, wherein the following conditional expression (10) is satisfied:

$$-3.0 < FL1G/IH < -1.0 \quad (10)$$

where,
FL1G denotes a focal length of the first lens unit in the first optical system and a focal length of the first lens unit in the second optical system.

19. The optical system for stereoscopic vision according to claim 8, wherein the following conditional expression (11) is satisfied:

$$1.5<FL2G/IH<7.0 \qquad (11)$$

where,
FL2G denotes a focal length of the second lens unit in the first optical system and a focal length of the second lens unit in the second optical system.

20. The optical system for stereoscopic vision according to claim 8, wherein the following conditional expression (12) is satisfied:

$$-10.0<FL3G/IH<20.0 \qquad (12)$$

where,
FL3G denotes a focal length of the third lens unit in the first optical system and a focal length of the third lens unit in the second optical system.

21. The optical system for stereoscopic vision according to claim 8, wherein the following conditional expression (13) is satisfied:

$$2.0<FL4G/IH<40.0 \qquad (13)$$

where,
FL4G denotes a focal length of the fourth lens unit in the first optical system and a focal length of the fourth lens unit in the second optical system.

22. The optical system for stereoscopic vision according to claim 8, wherein the stop is disposed in the second lens unit.

23. The optical system for stereoscopic vision according to claim 8, wherein the stop moves together with the third lens unit.

24. The optical system for stereoscopic vision according to claim 1, wherein the first optical system and the second optical system are the same optical system.

25. The optical system for stereoscopic vision according to claim 8, wherein the following conditional expression (14) is satisfied:

$$0.1<(MG1Gf/MG1Gn)/(MG3Gf/MG3Gn)<0.5 \qquad (14)$$

where,
MG1Gn denotes a lateral magnification of the first lens unit in the first optical system and a lateral magnification of the first lens unit in the second optical system at the time of focusing to the near point,
MG1Gf denotes a lateral magnification of the first lens unit in the first optical system and a lateral magnification of the first lens unit in the second optical system at the time of focusing to the far point,
MG3Gn denotes a lateral magnification of the third lens unit in the first optical system and a lateral magnification of the third lens unit in the second optical system at the time of focusing to the near point, and
MG3Gf denotes a lateral magnification of the third lens unit in the first optical system and a lateral magnification of the third lens unit in the second optical system at the time of focusing to the far point.

26. The optical system for stereoscopic vision according to claim 1, wherein the following conditional expression (15) is satisfied:

$$2.5<MGn/MGf<11.0 \qquad (15)$$

where,
MGn denotes a lateral magnification of the first optical system and a lateral magnification of the second optical system at the time of focusing to the near point, and
MGf denotes a lateral magnification of the first optical system and a lateral magnification of the second optical system at the time of focusing to the far point.

27. The optical system for stereoscopic vision according to claim 8, wherein the following conditional expression (16) is satisfied:

$$0.004<MG1Gn/MG1Gf<0.2 \qquad (16)$$

where,
MG1Gn denotes a lateral magnification of the first lens unit in the first optical system and a lateral magnification of the first lens unit in the second optical system at the time of focusing to the near point, and
MG1Gf denotes a lateral magnification of the first lens unit in the first optical system and a lateral magnification of the first lens unit in the second optical system at the time of focusing to the far point.

28. The optical system for stereoscopic vision according to claim 8, wherein the first lens unit in the first optical system and the first lens unit in the second optical system are integrated.

29. The optical system for stereoscopic vision according to claim 1, wherein the following conditional expression (17) is satisfied:

$$0.4<(a\tan(IH/FLf)/a\tan(IH/FLn))/(\theta f/\theta n)<0.85 \qquad (17)$$

where,
$\theta f$ denotes a half angle of view at the time focusing to a far point,
$\theta n$ denotes a half angle of view at the time of focusing to a near point,
FLf denotes a focal length of the first optical system and a focal length of the second optical system at the time of focusing to the far point, and
FLn denotes a focal length of the first optical system and a focal length of the second optical system at the time of focusing to the near point.

30. An image pickup apparatus, comprising:
an optical system; and
an imager which has an image pickup surface and which converts an image formed on the image pickup surface by the optical system to an electric signal,
wherein the optical system comprises the optical system for stereoscopic vision according to claim 1.

* * * * *